(12) United States Patent
Salzler

(10) Patent No.: US 11,747,340 B2
(45) Date of Patent: Sep. 5, 2023

(54) SYSTEMS AND METHODS FOR IDENTIFYING HLA-ASSOCIATED TUMOR PEPTIDES

(71) Applicant: Regeneron Pharmaceuticals, Inc., Tarrytown, NY (US)

(72) Inventor: Robert Salzler, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1202 days.

(21) Appl. No.: 16/361,342

(22) Filed: Mar. 22, 2019

(65) Prior Publication Data

US 2019/0293659 A1 Sep. 26, 2019

Related U.S. Application Data

(60) Provisional application No. 62/727,891, filed on Sep. 6, 2018, provisional application No. 62/702,981, filed on Jul. 25, 2018, provisional application No. 62/647,653, filed on Mar. 24, 2018.

(51) Int. Cl.

| | | |
|---|---|---|
| *G01N 33/68* | (2006.01) | |
| *C07K 1/22* | (2006.01) | |
| *C07K 1/36* | (2006.01) | |
| *C40B 30/04* | (2006.01) | |
| *G01N 33/569* | (2006.01) | |

(52) U.S. Cl.
CPC .......... *G01N 33/6842* (2013.01); *C07K 1/22* (2013.01); *C07K 1/36* (2013.01); *C40B 30/04* (2013.01); *G01N 33/56977* (2013.01); *G01N 33/6818* (2013.01); *G01N 33/6848* (2013.01); *G01N 2333/70539* (2013.01)

(58) Field of Classification Search
CPC .. C07K 1/22; C07K 1/36; G01N 2333/70539; G01N 33/56977; G01N 33/6818; G01N 33/6842; G01N 33/6848; C40B 30/04
See application file for complete search history.

(56) References Cited

PUBLICATIONS

Bailey et al., Intelligent data acquisition blends targeted and discovery methods. J Proteome Res. Apr. 2014;13(4):2152-61 (Year: 2014).*

(Continued)

*Primary Examiner* — Latosha Hines
(74) *Attorney, Agent, or Firm* — McCarter & English, LLP; Marcie B. Clarke

(57) ABSTRACT

Systems and methods for determining amino acid sequences of peptides that bind to MHC-I or HLA-I complex or MHC-II or HLA-II complex are provided. One embodiment includes isolating peptides from MHC or HLA class I or class II-peptide complexes and adding one or more known labeled peptides of interest to form a sample containing labeled peptides and unlabeled isolated peptides. The method also includes analyzing the sample with an LC-MS/MS system to obtain sequence data of the peptides, and increasing the sensitivity of the LC-MS/MS system when the labeled peptide is detected by the LC-MS/MS system. The method then concludes with determining the amino acid sequence of the unlabeled peptides in an m/z range that includes the m/z of the labeled peptide. The system can be triggered to increase the sensitivity in or near the m/z of the labeled peptide using an algorithm or computer program.

20 Claims, 9 Drawing Sheets

(56) References Cited

PUBLICATIONS

Caron et al., Analysis of major histocompatibility complex (MHC) immunopeptidomes using mass spectrometry. Mol Cell Proteomics. Dec. 2015;14(12):3105-17 (Year: 2015).*

Bailey et al., Intelligent data acquisition blends targeted and discovery methods. J Proteome Res. Apr. 2014;13(4):12152-61.

Caron et al., Analysis of major histocompatibility complex (MHC) immunopeptidomes using mass spectrometry. Mol Cell Proteomics. Dec. 2015;14(12):3105-17.

Sjostrom et al., A combined shotgun and targeted mass spectrometry strategy for breast cancer biomarker discovery. J Proteome Res. Jul. 2015;14(7):2807-18.

Venable et al., Automated approach for quantitative analysis of complex peptide mixtures from tandem mass spectra. Nat Methods. Oct. 2004;1(1):39-45.

White et al., Quantitative phosphoproteomic analysis of signaling network dynamics. Curr Opin Biotechnol. Aug. 2008;19(4):1404-9.

* cited by examiner

US 11,747,340 B2

SYSTEMS AND METHODS FOR IDENTIFYING HLA-ASSOCIATED TUMOR PEPTIDES

RELATED APPLICATIONS

This application claims the benefit of priority to U.S. Provisional Patent Application No. 62/647,653, filed on Mar. 24, 2018, U.S. Provisional Patent Application No. 62/702,981, filed on Jul. 25, 2018, and U.S. Provisional Patent Application No. 62/727,891, filed on Sep. 6, 2018. The entire contents of these applications are incorporated herein by reference.

TECHNICAL FIELD OF THE INVENTION

Aspects of the invention are generally related to the field of analytical chemistry, and the identification and sequencing of HLA-associated peptides.

BACKGROUND OF THE INVENTION

Human Papilloma Virus (HPV) is present in 100% of cervical and 20-40% of head and neck cancers (HNSCC) (Lowy et al., 2012). Like all intracellular and/or endogenously derived proteins, the viral proteins of HPV undergo proteolytic processing followed by presentation on Human Leukocyte Antigen (HLA) for immune surveillance by cytotoxic T lymphocytes (Angelika et al., 2010). Since HPV-derived proteins, such as the E7 oncogene, are only expressed in malignant cancer cells, these proteins are ideal targets for therapies.

Unfortunately, most current antibody therapeutics can only target membrane-based or soluble antigens. With respect to the selection of HLA-peptide targets that are expressed on the surface of cells, the field to date has relied on the availability of T cell receptors (TCRs) or on prediction algorithms. Mass spectrometry is the current tool of choice to access the physical presence of HLA-associated peptides in tissue. However, traditional mass spectrometry analysis detects the most abundant peptides in a sample and has a low level of specificity of peptides of lesser abundance. In many cases, peptides of interest have proven to be expressed at very low levels on tumor cells. Therefore, traditional mass spectrometry analysis is not sensitive enough to detect potentially beneficial peptide targets because they exist at such low levels.

Thus, there is a need for better tools to identify peptides presented by HLA on tumor cells, and measure their abundance.

SUMMARY OF THE INVENTION

The invention described herein provides a novel, extremely sensitive proteomic method to identify processed peptides presented by HLA-class I or HLA class II molecules. The disclosed systems and methods employ mass spectrometry to identify and sequence peptides of the human immunopeptidome using a labeled peptide of interest, wherein sensitivity of the mass spectrometer is increased when the labeled peptide is detected. By increasing the sensitivity of the system at specific times during an experimental run, peptides that would ordinarily go undetected can now be identified and sequenced. The novel method described herein is referred to as a "targeted trigger" mode of mass spectrometry (MS).

In one aspect, disclosed herein is a mass spectrometry method, the method comprising obtaining a sample comprising unlabeled isolated peptides from an MHC-I or HLA-I complex or an MHC-II or HLA-II complex; adding one or more labeled peptides to the sample to form a mixed sample comprising the labeled peptides and the unlabeled isolated peptides; processing the mixed sample with an LC-MS/MS system, comprising: i) processing the mixed sample in discovery mode to detect and identify one or more of the unlabeled isolated peptides and the one or more labeled peptides in the mixed sample; and ii) wherein, when the one or more labeled peptides are detected, processing the mixed sample with the LC-MS/MS system in targeted mode, thereby detecting and identifying the one or more labeled peptides.

In one embodiment, iii) wherein, when the one or more labeled peptides is no longer detected, the method further comprises processing the mixed sample with the LC-MS/MS system in discovery mode to detect and identify one or more of the unlabeled isolated peptides and the one or more labeled peptides in the mixed sample.

In one embodiment, iv) wherein, when the one or more labeled peptides are detected, the method further comprises processing the mixed sample with the LC-MS/MS system in targeted mode, thereby detecting and identifying the one or more labeled peptides.

In one embodiment, steps iii) and iv) are repeated 2 times, 3 times, 4 times, 5 times, 6 times, 7 times, 8 times, 9 times, 10 times, 11 times, 12 times, 13, times, 14 times, 15 times, 20 times, 25 times, 30 times, 35 times, 40 times, 45 times, or 50 times.

In another aspect, disclosed herein is a method of determining amino acid sequences of peptides that bind to an MHC-I or HLA-I complex or an MHC-II or HLA-II complex, comprising obtaining a sample comprising unlabeled isolated peptides from an MHC-I or HLA-I complex or an MHC-II or HLA-II complex; adding one or more labeled peptides to the sample to form a mixed sample comprising the labeled peptides and the unlabeled isolated peptides; continuously analyzing the mixed sample with an LC-MS/MS system to produce survey mass spectrometry scans of the sample, wherein detection of the one or more labeled peptides triggers a target label filter causing the system to scan isolated unlabeled peptides with a second mass spectrometer until the LC-MS/MS system does not detect the one or more labeled peptides.

In another aspect, disclosed herein is a method of determining amino acid sequences of peptides that bind to an MHC-I or HLA-I complex or an MHC-II or HLA-II complex, comprising obtaining a sample comprising unlabeled isolated peptides from an MHC-I or HLA-I complex or an MHC-II or HLA-II complex; adding one or more labeled peptides to the sample to form a mixed sample comprising the labeled peptides and the unlabeled isolated peptides; analyzing the mixed sample with an LC-MS/MS system to produce survey mass spectrometry scans of the sample; integrating into the LC-MS/MS system a target label filter based on the survey mass spectrometry scans to monitor a list of the one or more labeled peptides, thereby creating an integrated LC-MS/MS system; analyzing the mixed sample continuously with the integrated LC-MS/MS system, wherein detection of the one or more labeled peptides triggers the LC-MS/MS system to scan unlabeled isolated peptides until the integrated LC-MS/MS no longer detects the one or more labeled peptides; wherein the integrated LC-MS/MS system alternates between obtaining survey scans and scans of the one or more labeled peptides for the detection of endogenous peptides having the identical amino acid sequence of the one or more labeled peptides, respectively, and determining the amino acid sequence of the unlabeled isolated peptides scanned by integrated LC-MS/MS system.

In one embodiment, the survey mass spectrometry scans have a duration of about 100 ms. In one embodiment, the scan of the isolated unlabeled peptides has a duration of at least 400 ms. In one embodiment, the filter comprises an algorithm that increases scan duration when the labeled peptides are detected.

In one embodiment, the obtaining step comprises isolating the unlabeled peptides from an MHC-I or HLA-I complex or an MHC-II or HLA-II complex. In one embodiment, the isolating comprises affinity chromatography and/or column chromatography. In another embodiment, the isolating comprises isolating by affinity chromatography the MHC-I or HLA-I complex or the MHC-II or HLA-II complex obtained from a tissue lysate; separating peptides from the complexes by column chromatography to produce the unlabeled isolated peptides. In another embodiment, the isolating comprises passing a tissue lysate through an affinity chromatography column to produce a flow-through; eluting the column to produce a first eluate, wherein the first eluate comprises MHC-peptide complexes and beta2M associated peptides; passing the flow-through through a second affinity chromatography column to obtain a second eluate comprising MHC-peptide complexes and beta2M associated peptides; and independently eluting the peptides from the first and second eluates to produce unlabeled isolated peptides.

In one embodiment, the affinity chromatography comprises an anti-HLA I column. In one embodiment, the second affinity column comprises a pan HLA II column. In another embodiment, the column chromatography comprises use of a C18 reverse phase chromatography column.

In one embodiment, the sample comprising unlabeled isolated peptides is a tissue lysate. In one embodiment, the tissue lysate is produced using chemical and/or physical techniques. In one embodiment, the tissue lysate is produced from a tissue using a detergent. In one embodiment, the tissue lysate is produced from prostate tissue, breast tissue, testicular tissue, thyroid, colon tissue, ovarian tissue, pancreatic tissue, nervous tissue, bone, bone marrow, peripheral blood mononuclear cells, metastatic tissue, cancer cell lines, biopsies, or ocular tissue.

In one embodiment, the method further comprises determining an amino acid sequence of the unlabeled isolated peptides detected.

In one embodiment, a sequence of the unlabeled isolated peptides is determined in an m/z range that includes the m/z of the one or more labeled peptides.

In one embodiment, the labeled peptides are peptides labeled with heavy leucine, isoleucine, valine, threonine, lysine, tyrosine, phenylalanine, glycine, alanine, arginine, aspartic acid, or proline. In one embodiment, the heavy leucine is $(L)(^{13}C_6^{15}N_1)$.

In one embodiment, the method quantifies peptides present at a level of 30, 40, or 50 copies per cell or more.

In one aspect, disclosed herein is an LC-MS/MS system comprising a trigger filter that toggles between targeted mode and discovery mode when triggered. In one embodiment, the trigger filter is activated when one or more labeled peptides is detected.

In one aspect, disclosed herein is an unlabeled isolated peptide sequenced according to the methods described herein. In one embodiment, the peptide comprises at least one non-naturally occurring amino acid.

Methods to broadly sample and identify peptides of the immunopeptidome across tumor cells and tumor specimens, as well as normal (non-diseased) tissues, are provided. In some embodiments, the systems and methods quantify and sequence specific peptides of the tumor immunopeptidome.

One embodiment provides a method of determining amino acid sequences of peptides that bind to MHC-I or HLA-I complex or MHC-II or HLA-II complex by isolating peptides from MHC or HLA class I or class II-peptide complexes and adding one or more known labeled peptides of interest to form a sample containing labeled peptides and unlabeled isolated peptides. The method includes analyzing the sample with an LC-MS/MS system to obtain sequence data of the peptides, and increasing the sensitivity of the LC-MS/MS system when the labeled peptide is detected by the LC-MS/MS system. The method then concludes with determining the amino acid sequence of the unlabeled peptides in an m/z range that includes the m/z of the labeled peptide. The system can be triggered to increase the sensitivity in or near the m/z of the labeled peptide using an algorithm or computer program. In some embodiments the labeled peptide is labeled with a mass label for example a heavy isotope. In one embodiment, an algorithm or computer program triggers the LC-MS/MS to increase the scan duration time at or near the m/z of the labeled peptide to longer than 100 ms, and more typically to about 400 ms.

Another embodiment provides methods for identifying peptides presented by HLA (also referred to as MHC) in tumors that are "immunologically cold". Immunologically cold tumors include tumors that produce little or no immune response that results in the killing of tumor cells or the a reduction in tumor burden. The tumors can be from any tissue including, but not limited to tissues that can be surgically removed or ablated. Such tissues are referred to as "non-essential" tissue and include prostate, thyroid, and breast tissue to name a few. In one embodiment, the disclosed systems and methods can be used to identify new HLA-peptide targets (e.g., PRAME, KLK3/PSA) and prioritize other targets (e.g., HPV-E7 11-19 vs E7 82-90) for drug discovery. The disclosed systems advantageously require small amounts of tissue. In one embodiment the disclosed methods and systems can use about 40 mg to about 500 mg of tissue, about $1 \times 10^8$ cells, or about 100 mg of tissue.

Still another embodiment provides a method of determining amino acid sequences of peptides that bind to MHC-I (or HLA-I) complex or MHC-II (or HLA-II) complex including the steps of isolating by affinity chromatography peptides from a tissue lysate that specifically bind to MHC Class I or II complex, and labeling one or more of the isolated peptides with a detectable label to form samples containing labeled isolated peptides and unlabeled isolated peptides. An exemplary method includes continuously analyzing the sample with a first mass spectrometer of an LC-MS/MS system to produce survey mass spectrometry scans of the sample (discovery mode). The method includes integrating into the LC-MS/MS system a target label filter based on the survey mass spectrometry scans to monitor a list of selected labeled isolated peptides (target mode). In some embodiments, the method includes analyzing the samples with the integrated LC-MS/MS system, wherein detection of the labeled isolated peptides triggers the LC-MS/MS system to scan unlabeled isolated peptides with a second mass spectrometer to determine the sequence of the unlabeled peptides that are found in small quantity based on the detection of the labeled peptide (the "trigger"). Unlabeled peptides are sequenced until the integrated LC-MS/MS no longer detects the peptides that have the same mass of the labeled peptide. In this way, new peptides that bind to MHC-I or II complexes can be identified that share the same mass or have a similar mass to the known labeled peptides.

Another embodiment provides a method of determining amino acid sequences of peptides that bind to MHC-I complex or an MHC-II complex by isolating by affinity chromatography peptides from a tissue lysate that specifically bind to MHC Class I or II complex, and labeling one or more of the isolated peptides with a detectable label to form a sample containing labeled isolated peptides and unlabeled isolated peptides. The tissue sample is preferably a cancerous tissue sample. The method includes continuously analyzing the sample with first mass spectrometer of an LC-MS/MS system to produce survey mass spectrometry scans of the sample, wherein detection of labeled isolated peptides triggers a label filter causing the system to scan unlabeled isolated peptides having the same or similar mass of the labeled peptides with a second mass spectrometer until the LC-MS/MS system does not detect labeled isolated peptides. The method ends by determining the amino acid sequence of the unlabeled isolated peptides scanned by the LC-MS/MS system. In some embodiments, the sequenced peptides have different amino acid sequences than the labeled peptides and optionally different masses than the labeled peptides.

Another embodiment provides a method of determining amino acid sequences of peptides that bind to MHC-I complex or an MHC-II complex including the steps of isolating by affinity chromatography MHC-peptides obtained from a tissue lysate that specifically bind to MHC Class I or II complex and separating the peptides from the MHC-peptide complexes by column chromatography to produce isolated peptides. The method includes labeling one or more of the isolated peptides with a detectable label to form a sample containing labeled isolated peptides and unlabeled isolated peptides and continuously analyzing the sample with a first mass spectrometer of an LC-MS/MS system to produce survey mass spectrometry scans of the sample Detection of labeled isolated peptides triggers a label filter causing the system to scan unlabeled isolated peptides with a second mass spectrometer until the LC-MS/MS system does not detect labeled isolated peptides. The method ends by determining the amino acid sequence of the unlabeled isolated peptides scanned by the LC-MS/MS system.

Still another embodiment provides a method of determining amino acid sequences of peptides that bind to MHC-I complex or an MHC-II complex including the steps of passing a tissue lysate through an affinity chromatography column to produce a flow-through and eluting the column to produce a first eluate, wherein the first eluate comprises MHC-peptide complexes and beta2M associated peptides. The method also includes passing the flow-through through a second affinity chromatography column and obtaining a second eluate comprising MHC-peptide complexes and beta2M associated peptides. Next, the method includes independently eluting the peptides from the first and second eluates using a liquid chromatography column to produce isolated peptides and labeling one or more of the isolated peptides with a detectable label to form a sample containing labeled isolated peptides and unlabeled isolated peptides. The method includes analyzing the sample with an LC-MS/MS system to produce survey mass spectrometry scans of the sample. Detection of labeled isolated peptides triggers a label filter causing the system to scan unlabeled isolated peptides with a second mass spectrometer until the LC-MS/MS system does not detect labeled isolated peptides. The method concludes by determining the amino acid sequence of the unlabeled isolated peptides scanned by the LC-MS/MS system.

In some embodiments, the scan duration of the second mass spectrometer is sufficient to obtain the amino acid sequence of the unlabeled peptides. The scan duration can be longer than 100 ms, typically between 100 to 400 ms. Increasing the scan duration increases the sensitivity of the m/z range of labeled peptide and enables the detection of immunopeptidome peptides that are present in low copy number.

In one embodiment, the detectable label is a heavy isotope labeled amino acid. In some embodiments, the detectable label is a heavy amino acid selected from heavy leucine, isoleucine, valine, threonine, lysine, tyrosine, phenylalanine, glycine, alanine, arginine, aspartic acid, and proline. In other embodiments, the detectable label is leucine (L)($^{13}C_6^{15}N_1$).

Exemplary affinity chromatography columns that can be used include but are not limited to anti-HLA I and anti-HLA II columns.

In some embodiments the isolated peptides are obtained using a C18 reverse phase column eluted with a 30% acetonitrile mobile phase.

In some embodiments the lysate is produced from prostate tissue, breast tissue, testicular tissue, colon tissue, thyroid, ovarian tissue, pancreatic tissue, nervous tissue, bone, bone marrow, peripheral blood mononuclear cells, metastatic tissue, cancer cell lines, biopsies, and ocular tissue.

DETAILED DESCRIPTION OF THE INVENTION

Figure 1:
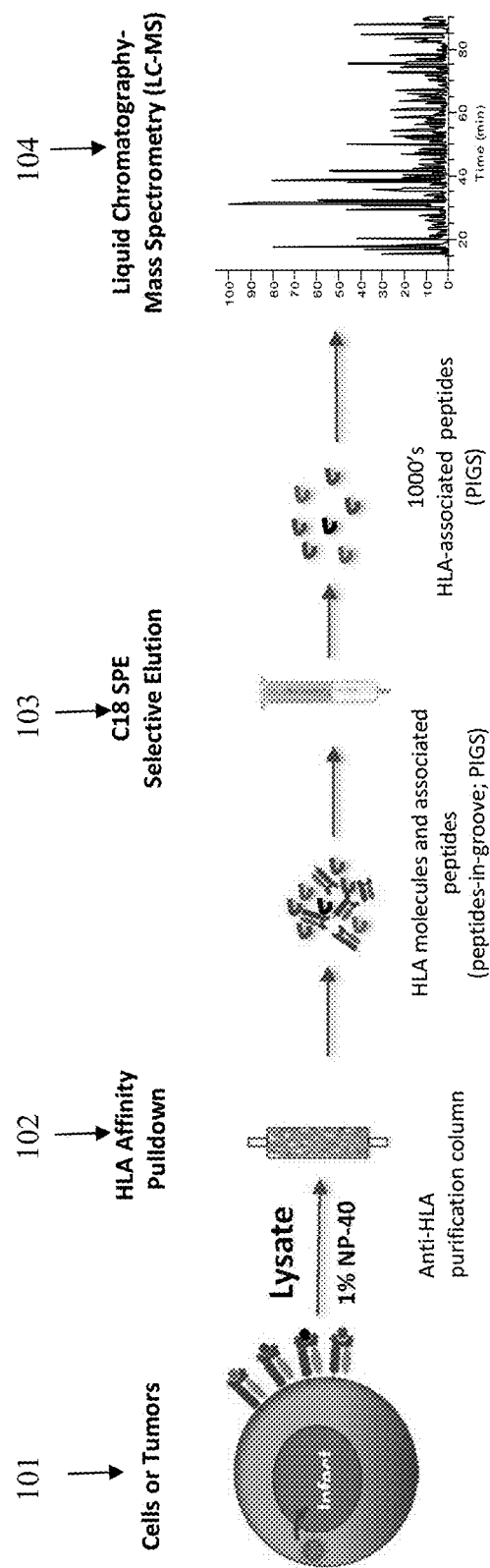
FIG. 1 is a diagram of an exemplary method for identifying proteins in the groove (PiGs) of MHC-I or MCH-II. An exemplary cell line used was a Caski HPV16+ cervical cell line.

In some aspects, the present invention is based, at least in part, on improved systems and methods for identifying peptides that bind to HLA or MHC. Prior to the instant invention, mass spectrometry was used in either one of two ways: a targeting mode, where a specific targeted peptide(s) is measured; or a discovery mode "shotgun," which uses lower sensitivity for identification of many peptides, without discrimination of specific targets, in a sample. Prior to the instant invention, it was believed that toggling between the targeting mode and the discovery mode using a single sample was not possible within a short timeframe (i.e., milliseconds) and/or without experiencing any loss of data. Therefore, prior to the instant invention one skilled in the art would have been forced to choose between a less sensitive discovery mode to capture as many peptides as possible, which could cause the peptide of interest to be missed, or use a more sensitive mode that targets only known peptides of interest, which prevents detection of peptides that would have been found in discovery mode. Prior to the instant invention, there was no way to capture the immunopeptidome while simultaneously being able to target specific peptides of low sensitivity by spending more time (additional milliseconds) on those targeted peptides. This toggling allows more, better, and quantitative information to be obtained from a single, precious patient sample, than either the discovery or targeted mode alone.

As described herein, the disclosed novel systems and methods employ mass spectrometry to identify and sequence peptides of the human immunopeptidome using a labeled peptide of interest, wherein sensitivity of the mass spectrometer is increased when the labeled peptide is detected. By increasing the sensitivity of the system at specific times during the experimental run, peptides that would ordinarily go undetected can now be identified and sequenced. The novel methods described herein are referred to as a "targeted trigger" mode of mass spectrometry (MS).

In the novel targeted trigger mode described herein, a sample is spiked with a known labeled (e.g., heavy) peptide, and the system is run in a "targeted" mode. Once the labeled peptide is no longer detected, the system switches to a "discovery" mode, which allows for identification of endogenous (non-labeled) peptides in the sample. The mass spectrometry instrument toggles between the targeted mode and the discovery mode allowing for collection of data relating to the immunopeptidome in both target and discovery modes in a single sample. In other words, the present disclosure provides a targeted trigger method that combines a MS peptide discovery mode, which detects all of the possible peptides in a sample, with a targeted mode, by toggling between the two modes based on identification of a known peptides which is "spiked" into the sample, within the same run and without the loss of data. In some embodiments, up to 5, 6, 7, 8, 9, 10, 25, 50, 75, 100, more than 100, or about 500 switches between targeted and discovery modes can be carried out using a single sample. The limit on how many switches are desirable is based on how many endogenous peptides of interest are expected to be in the sample. The time increases by milliseconds with each heavy peptide, but the time spent on each heavy peptide is only about 400 milliseconds so that the time increase is not a critical consideration relative to the limited number of targets. There are many moderate level and important peptides found in discovery mode, but the instant invention enables the sensitivity to be increased on low abundant peptides during a discovery mode that spends about 100 milliseconds on each non-targeted peptide. In one embodiment, there are approximately 50 heavy peptides spiked in a sample. In another embodiment, there are more than 40, there are about 50-60, there are about 50-70 heavy peptides spiked in a sample.

The disclosed systems and methods provide several advantages over other mass spectrometry methods for identifying peptides. In particular, the disclosed systems and methods can advantageously get more information from small sample sizes than other mass spectrometry methods, and can detect peptides of the immunopeptidome that are expressed at low copy numbers while simultaneously detecting many other, higher copy number peptides from the sample. For example, the combination of the discovery and targeted modes allows for increased sensitivity in detecting a target of interest using the targeted mode, while also providing for identification of novel targets using the discovery mode using a single sample. Tumor samples are valuable and are often not readily available. The targeted trigger methods of the invention provide access to the maximum amount of information from one LC-MS analysis of one sample, in a short timeframe, thus allowing for savings in cost and time and preserving valuable tumor sample.

The newly identified peptides using the discovery mode can be used to develop vaccines and immunotherapies against autoimmunity, infectious diseases and cancers. Exemplary immunotherapies that can be developed using the newly identified peptides include, but are not limited to CAR T cells, bispecific antibodies, and antibody-drug conjugates.

The disclosed systems and methods described herein also provide detection of post-translational modifications (PTMs) on identified peptides. The patterns of PTMs on peptides from normal proteins or aberrant proteins (e.g., proteins in tumor tissues) provide important information about specific immune responses in cancers and the certain post-translationally modified peptides may serve as tumor-specific targets for next-generation immunotherapies.

Existing MS platforms require 1 gram of tissue to detect hundreds to thousands of MHC class I peptides (Dutoit, V., et al., Brain 135, 1042-1054 (2012)). However, in one embodiment, the sample size analyzed in the methods of the invention is typically less than 1.0 g, about 0.5 grams or less. Without the targeted trigger mode, the targeted peptide would not be found in 0.5 grams of tumor tissue.

Low copy number refers to peptides that are presented on the cell surface in the context of HLA at about 100 copies or less per cell. In one embodiment, the peptides are present at 50 to 60 copies per cell. In one embodiment, the peptides are present at 40 to 50 copies per cell. In one embodiment, the peptides are present at 30 to 40 copies per cell. For example, most HPV+ samples have less than 100 copies per cell of peptides of interest. Moderate 100-400 copies per cell. Low copy number (e.g., less than 100 copies per cell) peptides are missed in discovery mode because the discovery mode sensitivity is not sufficient to identify them. Said differently, low copy number peptides would be missed in discovery mode, and the present invention, allows them to be detected in targeted trigger mode.

I. Definitions

As used herein, the term "discovery mode" refers to a method of mass spectrometry analysis wherein all peptides in a sample are detected. Discovery mode may detect endogenous, unlabeled peptides in a sample. Discovery mode is discussed in more detail herein.

As used herein, the term "targeted mode" or "targeting mode" refers to a mass spectrometry method of analysis wherein a known peptide(s) in a sample is identified using a labeled peptide(s) which is "spiked" into the sample. Targeted mode is discussed in more detail herein.

As used herein, the term "targeted trigger" mode refers to a method of mass spectrometry that combines a discovery mode with a targeted mode by toggling between the two modes based on identification of a known peptide(s) which is "spiked" into a sample. Targeted trigger mode is discussed in more detail herein.

"LC-MS/MS" refers to liquid chromatography-tandem mass spectrometry. LC-MS/MS is an analytical chemistry technique that combines liquid chromatography with mass spectrometry for physical separation and mass analysis of samples.

"MS1" and "MS2" refers to the two sequential mass spectrometry analyses that are performed on samples during tandem mass spectrometry analysis. Peptide precursors are first identified in the MS1 scan and one or more peaks are then selected for subsequent fragmentation to generate their corresponding MS2 spectra. Generally, MS1 separates the sample based on their mass-to-charge ratio (m/z).

"Processed peptides" refer to protein fragments of intracellular origin which are degraded by a protease(s). The protein fragments can be truncated into smaller peptides and translocated into the endoplasmic reticulum for assembly of the peptide-HLA complex.

The terms "HLA" and "MHC" are used interchangeably. Major histocompatibility complex (MHC) is found in vertebrates, while human leukocyte antigen (HLA) is only found in humans. Both sets of proteins encode cell surface molecules that are specialized to present antigenic peptides to T cell receptors on T cells.

The term "post-translational modification" or "PTM" refers to covalent and generally enzymatic modification of proteins following protein biosynthesis. Proteins synthesized by ribosomes may then undergo PTM to form the mature protein product. PTMs are important components in cell signaling, as for example when prohormones are converted to hormones. Furthermore, PTMs play a critical role in the etiology of cancer and other diseases.

The term "aberrant" refers to any amino acid mutation(s) or post-translational modification(s) on a protein or peptide in a tissue, e.g., a tumor tissue that is different from a healthy tissue. For example, an aberrant protein may have one or more amino acid mutations compared to a normal protein in a healthy tissue. Peptides from an aberrant protein may have different types of PTMs compared to a normal protein in a healthy tissue. Peptides from an aberrant protein may have different levels of certain PTMs compared to a normal protein in a healthy tissue.

The term "PiG" refers to peptide in the groove. Peptides with adequate binding motif residues can bind into the peptide binding groove of HLA molecules. Binding of peptides with the groove of HLA allows the assembled molecule to leave the endoplasmic reticulum and be transported to the cell surface to display the peptides to T cells.

HPV16E7 has the following amino acid sequence: MHGDTPTLHEYMLDLQPETTDLYCYEQLNDSSEEE-DEIDGPAGQAEPDRAHYNIVTFCC KCD-STLRLCVQSTHVDIRTLEDLLMGTLGIVCPICSQKP (SEQ ID NO: 1). HPV16E7$_{11-19}$ refers to the following peptide sequence: YMLDLQPET (SEQ ID NO:2). HPV16 E7$_{11-19}$ and HPV E7$_{11-19}$ are equivalent. It is well established that strains of HPV, including but not limited to HPV16+ strains, are associated with cervical cancer risk Burd, E., Clin Micobiol. Rev., 16(1):1-17 (2003).

II. Methods for Mining the HLA-Peptidome

The human immunopeptidome or HLA immunopeptidome refer to the array of endogenous peptides that bind to HLA. Human leukocyte antigen (HLA) class I molecules expose the health status of cells to CD8+ cytotoxic T lymphocytes (CTLs) by presenting at the surface of each cell around $10^4$ different peptide species (with varying copy numbers) processed from the cellular protein content. CTLs can eradicate cells infected with microbial pathogens and cancer cells upon recognition of pathogen-derived or tumor-specific peptides. However, CTLs also cause tissue damage in autoimmune disease if derailed T cells are reactive with self-protein-derived peptides. The T-cell receptor (TCR) mediates the specificity of recognition by binding to the HLA class-I-presented short peptide (length 8-12 amino acids), also called class I ligand, or CTL epitope when recognized by CTLs. Together, all class I ligands of a cell constitute the self class I immunopeptidome.

The mechanisms of HLA class I antigen processing include enzymatic degradation by the proteasome and peptidases, intracellular routing, and specific binding to the individual's highly polymorphic HLA class I molecules. Canonical HLA class I ligands are liberated during a first digestive step from their source in the channel of the complex multi-subunit and multi-catalytic proteasome. Proteasomal degradation has a stochastic nature but follows rules allowing its predictive modeling.

One embodiment provides a method of determining amino acid sequences of peptides that bind to MHC-I or HLA-I complex or MHC-II or HLA-II complex by isolating peptides from MHC or HLA class I or class II-peptide complexes and adding one or more known labeled peptides of interest to form a sample containing labeled peptides and unlabeled isolated peptides. The method includes analyzing the sample with an LC-MS/MS system to obtain sequence data of the peptides, and increasing the sensitivity of the LC-MS/MS system when the labeled peptide is detected by the LC-MS/MS system. The method then concludes with determining the amino acid sequence of the unlabeled peptides in an m/z range that includes the m/z of the labeled peptide. The system can be triggered to increase the sensitivity in or near the m/z of the labeled peptide using an algorithm. In some embodiments the labeled peptide is labeled with a mass label for example a heavy isotope. In one embodiment, an algorithm triggers the LC-MS/MS to increase the scan duration time at or near the m/z of the labeled peptide to longer than 100 ms, and more typically to about 400 ms.

A. Sample Preparation

In one embodiment, the sample is procured from tumor tissue or cancerous tissue. The tissue can be tissue that is surgically removed or ablated. In one embodiment, the tissue is from "non-essential" tissue such as prostate tissue, breast tissue, testicular tissue, colon tissue, thyroid, ovarian tissue, pancreatic tissue, nervous tissue, bone, bone marrow, peripheral blood mononuclear cells, metastatic tissue, cancer cell lines, biopsies, and ocular tissue. The sample can also be procured from cell lines.

The disclosed systems and methods can be used to obtain valuable data from small samples, for example from about 40 grams to about 500 grams of tissue or about $1\times10^6$ to about $2\times10^8$ cells, typically about $1\times10^7$ cells or $1\times10^8$ cells. For example, 1 gram of liver tissue is about $1\times10^8$ cells. Other tissues have different numbers of cells. For example, 1 gram of fat tissue has fewer numbers of cells and protein than 1 gram of liver tissue. In one embodiment, the sample can be 1 gram, 0.9 grams, 0.8 grams, 0.7 grams, 0.6 grams, 0.5 grams, 0.4 grams, 0.3 grams, or 0.2 grams or less, of tissue, such as a biopsy. In another embodiment, the sample can be less than 0.5 grams of tissue. As sample size is reduced, the number of peptides is also reduced. Therefore, the number of endogenous peptide of interest also can be reduced. The target peptide will always be identified, but if the sample size is too small, then there may not be enough endogenous peptide of interest to be detected by the machine.

Each tissue is different, each tumor is different, and each peptide of interest is regulated differently in the tissue. But for example, in 0.5 gram tissue there may be 7000 peptides, in half that size, maybe 4000 peptides. Even with targeted trigger mode, the peptide might not be found if the sample is too small or if the endogenous peptide of interest is not there, which can be informative as well.

The sample can be from a primary tissue, a frozen sample of tissue, lyophilized tissue, a biological fluid, or a combination thereof. In one embodiment the tissue is powdered on dry ice and lysed for example in a buffer. Lysis buffers are well known in the art. See, for example Babu, V. et al., J Gen Eng Biotech, 11(2):117-122 (2013). The lysis buffer typically contains a detergent and is often used in conjunction with homogenization and/or mechanical disruption. The detergent can be ionic, non-ionic, or zwitterionic. An exemplary lysis buffer contains two ionic detergents and one nonionic detergent in Tris buffer: 25 mM Tris-HCl, pH 7.6, 150 mM NaCl, 1% NP40, 1% sodium deoxycholate and 0.1% sodium dodecyl sulfate (SDS). In one embodiment, the lysis buffer contains NP-40 with HALT protease and phosphatase inhibitors (Thermo Scientific, cat. 78442) on ice.

In one exemplary embodiment, the solution can be further mechanically disrupted, for example using a tissue raptor to generate a homogenous lysate. The lysate can be rotated for a period of time, for example 1 hour at 4° C. followed by a 30-minute centrifugation, for example at 20,913 g at 4° C. Lysates can then be passed over an affinity column, for example an in-house pan HLA-Class I affinity column (1 ml column, 4 mg of total antibody on beads). Captured HLA-peptide complexes can be eluted with, for example, 4 mLs of glycine pH 2.5. In some embodiments, trifluoroacetic acid (TFA), e.g., one ml of 0.1% TFA can be added to the eluate before passing through a reverse phase chromatography media, e.g., a Sep Pak tC18 1 CC cartridge (Waters, Cat. WAT054960). The cartridge can be washed, e.g., 3 times with 1 mL of 0.1% TFA. The bound peptides can be selectively eluted from the tC-18 cartridges using, for example, 30% acetonitrile (ACN) in 0.1% TFA. In some embodiments, the eluted peptides can be speedvac dried and re-suspended into 20 μl of 0.1% TFA (along with heavy spike-in peptides) for LC-MS/MS analysis. (See FIG. 1).

1. Mass Labels

In one embodiment, known labeled peptides are spiked into the sample of unlabeled isolated peptides. The labeled peptides can be mass labeled with an isotopically heavy amino acid. Any amino acid that is in the known amino acid sequence of the peptide can be labeled using stable isotope labeling. The method relies on the substitution of an amino acid with an amino acid with stable isotopic nuclei, for example deuterium, $^{13}C$, and $^{15}N$. In an embodiment, the amino acid that is labeled is leucine, isoleucine, valine, threonine, lysine, tyrosine, phenylalanine, glycine, alanine, arginine, aspartic acid, or proline. It will be appreciated that any available heavy amino acid can be used. Heavy isotope amino acids are available from multiple vendors such as AnaSpec. An exemplary isotopically heavy amino acid is leucine (L)($^{13}C_6{}^{15}N_1$). In one embodiment, the isotopic label does not affect the peptide retention time in the LC. Labeled and unlabeled peptides must have the same retention time for the methods disclosed herein.

In one embodiment, a known amount of mass labeled peptide is spiked into the sample of unlabeled isolated peptides. The amount of mass labeled peptide to be spiked into the unlabeled isolated peptide can be between 50 fmol and 100 fmol. The amount of mass labeled peptide to be spiked into the unlabeled isolated peptide can be 50, 55, 60, 65, 70, 75, 80, 85, 90, 95, or 100 fmol. In one embodiment, the amount of mass labeled peptide can be used to determine the relative copy number of a peptide in a sample.

B. LC-MS/MS Analysis of HLA Class I Peptides

The peptides in the sample may be purified or isolated, for example, using liquid chromatography. Liquid chromatography is a technique used to separate a sample into its individual parts. This separation occurs based on the interactions of the sample with the mobile and stationary phases. Because there are many stationary/mobile phase combinations that can be employed when separating a mixture, there are several different types of chromatography that are classified based on the physical states of those phases. Liquid-solid column chromatography, the most popular chromatography technique features a liquid mobile phase which slowly filters down through the solid stationary phase, bringing the separated components with it. The types of chromatography that can be used include, but are not limited to normal phase chromatography, reverse phase chromatography, flash chromatography, partition chromatography, liquid-solid chromatography, ion exchange chromatography, size exclusion chromatography, affinity chromatography, chiral chromatography, or combinations thereof.

Liquid phases or mobile phases for liquid chromatography are known in the art and one of skill in the art could modify the mobile phase to separate the peptide sample into component parts.

1. Affinity Chromatography

Figure 2A:
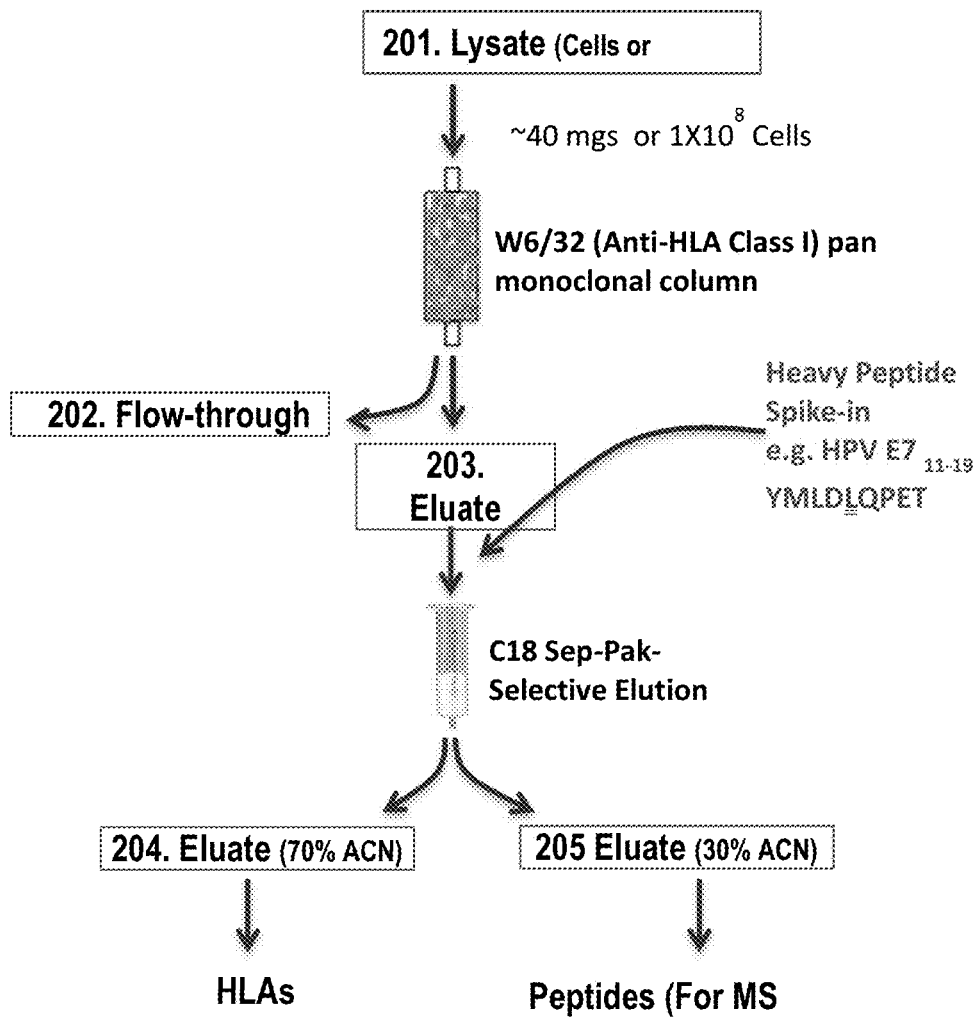
FIG. 2A represents an example of an "immune affinity enrichment workflow" and provides a diagram of an exemplary method for separating MHC-I-associated peptides or MHC-II associated-peptides using affinity chromatography and mass spectrometry analysis.
Figure 2B:
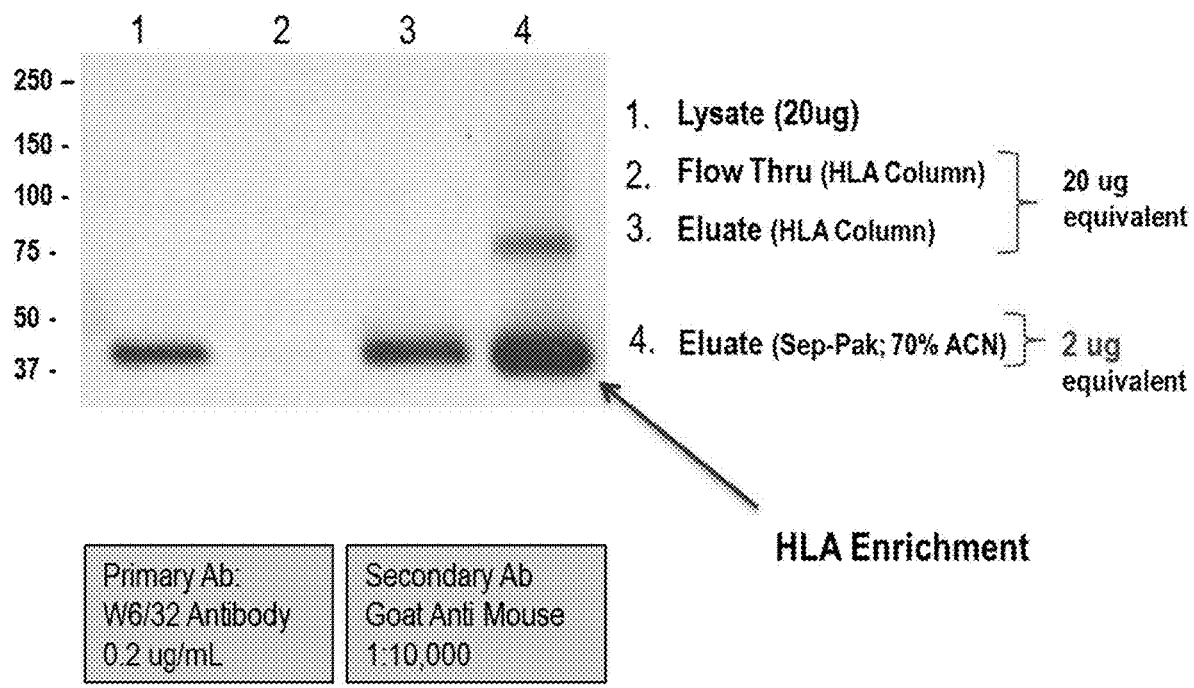
FIG. 2B shows a Western blot of the peptides separated by the method in FIG. 2A. Primary antibody used was W6/32 antibody at 0.2 g/mL. Secondary antibody was goat anti-mouse at 1:10,000.

In some embodiments, the present invention includes use of an affinity chromatography medium to isolate peptide-HLA complexes. As depicted in FIG. 2A, a cell lysate prepared as described herein can be passed through an affinity column (such as an anti-HLA Class I pan monoclonal column). After elution of the column, the eluate containing peptide-HLA complexes is collected (203 of FIG. 2A).

Affinity chromatography (also called affinity purification) makes use of specific binding interactions between molecules. A particular ligand is chemically immobilized or "coupled" to a solid support so that when a complex mixture is passed over the column, those molecules having specific binding affinity to the ligand become bound. After other sample components are washed away, the bound molecule (e.g., the peptide-HLA complex) is stripped from the support, resulting in its purification from the original sample.

Most commonly, ligands are immobilized or "coupled" directly to solid support material by formation of covalent chemical bonds between particular functional groups on the ligand and reactive groups on the support. Ligands that bind to general classes of proteins are commercially available in pre-immobilized forms ready to use for affinity purification.

Most affinity purification procedures involving protein: ligand interactions use binding buffers at physiologic pH and ionic strength, such as phosphate buffered saline (PBS). This is especially true when antibody:antigen or native protein: protein interactions are the basis for the affinity purification. Once the binding interaction occurs, the support is washed with additional buffer to remove non-bound components of the sample. Nonspecific (e.g., simple ionic) binding interactions can be minimized by adding low levels of detergent or by moderate adjustments to salt concentration in the binding and/or wash buffer. Finally, elution buffer is added to break the binding interaction and release the target molecule (e.g., the peptide-HLA complex) which is then collected in its purified form.

Elution buffers dissociate binding partners by extremes of pH (low or high), high salt (ionic strength), the use of detergents or chaotropic agents that denature one or both of the molecules, removal of a binding factor or competition with a counter ligand. In some embodiments, the elution buffer is glycine, at, e.g., pH 2.5. Other buffers may include 0.1% formic acid or 0.1% trifluoroacetic acid (TFA).

In principle, any buffer substance can be used in the methods as reported herein. In one aspect, a pharmaceutically acceptable buffer substance is used with the affinity chromatography medium, such as e.g., phosphoric acid or salts thereof, acetic acid or salts thereof, citric acid or salts thereof, morpholine, 2-(N-morpholino) ethanesulfonic acid (MES) or salts thereof, histidine or salts thereof, glycine or salts thereof, tris(hydroxymethyl)aminomethane (TRIS) or salts thereof, (4-(2-hydroxyethyl)-1-piperazineethanesulfonic acid (HEPES) or salts thereof.

In one aspect, the buffer substance is selected from phosphoric acid or salts thereof, or acetic acid or salts thereof, or citric acid or salts thereof, or histidine or salts thereof.

In one aspect, two buffer substances are used. In one aspect, the buffer substance in the first solution and the buffer substance in the second solution are the same buffer substance. In one aspect the buffer substance in the first solution and the buffer substance in the second solution are different buffer substances.

In one aspect of the invention, the affinity chromatography medium used in the methods of the invention is coupled with one or more additional chromatography media, such as a reverse phase chromatography medium. In another aspect, the one or more chromatography media of the invention are coupled directly to mass spectrometry (MS).

2. Reverse Phase Chromatography

In some embodiments, peptide-HLA complexes are spiked with a heavy peptide that is known to bind to the HLA-I complex or is of a desired mass. The spiked sample is then passed through a reverse phase column, for example, a C18 Sep-Pak column, and peptides for mass spectrometry analysis are selectively eluted.

Reverse phase liquid chromatography (RPC or RPLC), also referred to as hydrophobic chromatography, includes any chromatographic method that uses a hydrophobic stationary phase. Reverse phase chromatography is a technique using alkyl chains covalently bonded to the stationary phase particles in order to create a hydrophobic stationary phase, which has a stronger affinity for hydrophobic or less polar compounds. In RPC, a molecule in solution binds to the hydrophobic surface or hydrophobic ligand of a chromatographic resin. The partitioning of the molecule between the solution and the resin occurs as a result of hydrophobic interactions between the molecule with hydrophobic patches at its surface and the hydrophobic surface on the resin. A solvent of increasing hydrophobicity is subsequently used to dissociate or elute the bound molecule at a point at which the hydrophobic interaction between the exposed patches and the resin is less favorable than the interaction between the bound molecule and the solvent. The molecule then releases from the resin and elutes. Separation of different molecules in the same solution occurs if the molecules have different hydrophobicity and therefore elute at different point in time when the hydrophobicity of the eluting solvent is increased.

In general, RPC is capable of distinguishing between molecules with very small differences in hydrophobicity and it is thus regarded as a powerful separation tool and a preferred method in analytical chromatography.

RPC column medium is made of a resin to which as hydrophobic material may be attached. Stationary phases for reverse phase chromatography include, but are not limited to, silylated silica (i.e., wherein silica has been treated with $RMe_{2SiCl}$, and wherein R is a straight chain alkyl group such as $C_{18}H_{37}$, $C_8H_{17}$, or $C_4H_7$), diphenyl resins, divinylbenzene resins, and carbon resins. Another typical resin material is polystyrene; hydrophobic ligands may optionally be attached. In case of substituted resins, the resin is substituted with a hydrophobic ligand, typically selected from (but not limited to) aliphates, such as $C_2$, $C_4$, $C_6$, $C_8$, $C_{10}$, $C_{12}$, $C_{14}$, $C_{16}$, or $C_{18}$ or derivates of these, e.g., cyanopropyl (CN-propyl), or branched aliphates, or benzene-based aromates, such as phenyl, or other polar or non-polar ligands. The ligand may be a mixture of two or more of these ligands. Suitable polystyrene based resins include, without limitation, resins supplied by Rohm Haas (e.g., Amberlite XAD or Amberchrom CG), Polymer Labs (e.g., PLRP-S), GE Healthcare (e.g., Source RPC), Applied Biosystems (e.g., Poros R).

In certain aspects, reverse phase chromatography includes the use of a graphitized-carbon resin (e.g., porous graphitized carbon, PGC).

The manufacturing processes for and optimal features of the RPC material often require that a linking group, also called a spacer, is inserted between the resin and the ligand.

Features for RPC media which improve performance with large proteins such as antibodies include, for example, wide-pore phases, such as organic monoliths with macropore sizes of between about 1-5 μm, core-shell particles of about 2.5-5 μm, and fully porous sub-2 μm UHPLC columns.

Typical mobile phases for reverse phase chromatography include relatively polar elution buffer solutions, such as water and polar organic solvents (e.g., acetonitrile, organic alcohols). Retention time is increased by the addition of polar solvent to the mobile phase and decreased by the addition of more hydrophobic solvent. The retention time is therefore longer for analytes which are more non-polar in nature, allowing polar analytes to elute more readily.

In one aspect, a buffer is a mixture of an acid (HA) and its conjugated base ($A^-$). A buffer is capable of resisting changes in pH as the result of addition of acid or base. This resistance (buffer capacity) is largest when pH is close to the pKa of the acid HA. A mixture of an acid and the conjugated base is regarded as a buffer if the pH of the solution is within two pH units, such as within one pH unit from the pKa value of the acid. Examples of buffers which can be applied in the present invention include acetate buffers, phosphate buffers, citric acid buffers, lactic acid buffers, TRIS buffers, CHAPS buffers, borate buffers, HEPES buffers, carbonate buffers, histidine buffers, MES buffers, ascorbic buffers, and mixtures of two or more of these. It is standard in the art to add trifluoro acetic acid (TFA) to RPC solvents to adjust pH.

In some embodiments, the elution buffer used in the methods of the invention is acetonitrile (ACN) in TFA, e.g., 30% acetonitrile (ACN) in 0.1% TFA.

Typically pH of solvents is within the range of 1-13, such as 2-13, such as 3-13, such as 3.5-13, such as 4-13, such as 4.5-13, such as 5-13, such as 5.5-13, such as 6-13, such as 6.5-13, such as 7-13, such as 7.5-13, such as 8-13, such as 1-12, such as 1-11, such as 1-10, such as 1-9.5, such as 1-9, such as 1-8.5, such as 2-10, such as 3-9.5, such as 3.5-9.5, such as 4-9.5, such as 4.5-9.5, such as 5-9.5, such as 5.5-9.5, such as 6-9.5, such as 6.5-9.5, such as 7-9.5, such as 7.5-9.5, such as 8-9.5, such as 3-9, such as 3.5-9, such as 4-9, such as 4.5-9, such as 5-9, such as 5.5-9, such as 6-9, such as 6.5-9, such as 7-9, such as 7.5-9, such as 8-9, such as 3-8.5, such as 3.5-8.5, such as 4-8.5, such as 4.5-8.5, such as 5-8.5, such as 5.5-8.5, such as 6-8.5, such as 6.5-8.5, such as 7-8.5, such as 7.5-8.5, such as 8-8.5, such as 3-8, such as 3.5-8, such as 4-8, such as 4.5-8, such as 5-8, such as 5.5-8, such as 6-8, such as 6.5-8, such as 7-8, such as 7.5-8.

In one aspect, the solvent used to elute the peptides comprises a salt in solution. The term salt is used for ionic compounds composed of positively charged cations (X) and negatively charged anions (Y), so that the product is neutral and without a net charge. Both X and Y may be multiply charged so that the ratio X:Y may be different from 1:1.

The salt used together with the buffer does not have any significant buffering capacity at the pH achieved with the specific buffer used and are thus not part of the buffer system itself. In one aspect, the pKa of the salt is at least one pH unit removed from the pKa of the buffer used. In a further aspect, the pKa of the salt is at least one pH unit removed from the pKa of the buffer used. The choice of salt to be used together with the buffering system will naturally depend on the choice of buffer, but when working at a pH range usual for handling proteins, examples of salts which can be applied in the present invention could include halides, such as chlorides, bromides, iodines; sulphates; borates; lactates; and citrates, and mixtures of two or more thereof. Examples of the positively charged counter ion include sodium; potassium; magnesium; calcium; and ammonium. Specific examples of salts include potassium chloride; sodium chloride; ammonia chloride and potassium lactate.

In one aspect, the elution buffer solution used in the methods of the present invention comprises an aqueous solvent comprising water and an organic component. Typical organic components include acetonitrile or alcohols.

In one aspect, the organic component is an alcohol, and in one aspect, the solvent is a mixture of water and an alcohol. Particular mentioning is made of mono-alcohols, i.e. alcohols comprising only one alcohol group. Examples of mono-alcohols which can be used in the methods of the present invention include methanol, ethanol, 1-propanol and 2-propanol, and mixtures of two or more thereof. In another aspect, the organic component is acetonitrile, and in one aspect, the solvent is a mixture of water and acetonitrile.

Another important component is pH since this can change the hydrophobicity of the analyte. For this reason most methods use a buffering agent, such as sodium phosphate to control the pH. An organic acid such as formic acid or trifluoroacetic acid is often added to the mobile phase. These serve multiple purposes by controlling the pH, neutralizing the charge on any residual exposed silica on the stationary phase and acting as ion pairing agents to neutralize charge on the analyte. The effect varies depending on use but generally improves the chromatography.

In one aspect of the invention, two buffer solutions are used for elution. In one aspect, the buffer substance in the first solution and the buffer substance in the second solution are the same buffer substance. In one aspect the buffer substance in the first solution and the buffer substance in the second solution are different buffer substances.

In one aspect of the invention, the reverse phase chromatography medium is coupled online with one or more additional chromatography media, such as an affinity chromatography medium, as described in detail herein. In another aspect, the chromatography media of the invention can be coupled directly to mass spectrometry (MS) using methods known to one of ordinary skill in the art.

3. Mass Spectrometry

Once the peptides are separated using LC or other methods known to those of ordinary skill in the art, the peptides are analyzed with mass spectrometry to obtain the mass of the peptides and the amino acid sequence of the peptides. The two primary methods that can be used for the ionization of protein in mass spectrometry are electrospray ionization (ESI) and matrix-assisted laser desorption/ionization (MALDI). These ionization techniques are used in conjunction with mass analyzers such as tandem mass spectrometry.

Tandem mass spectrometry (MS/MS) is used to measure fragmentation spectra and identify proteins at high speed and accuracy. Collision-induced dissociation is used in mainstream applications to generate a set of fragments from a specific peptide ion. The fragmentation process primarily gives rise to cleavage products that break along peptide bonds. Because of this simplicity in fragmentation, it is possible to use the observed fragment masses to match with a database of predicted masses for one of many given peptide sequences. Tandem MS of whole protein ions has been investigated recently using electron capture dissociation and has demonstrated extensive sequence information in principle but is not in common practice.

Several mass spectrometry based platforms can be used with the disclosed methods (Caron, E., et al., Molecular & Cellular Proteomics 14.12 (2015). (1) data dependent analysis DDA, (2) targeted data acquisition, and (3) data-independent acquisition (DIA). DDA is a well-established and a widely used method for large-scale identification of MHC-associated peptides. In DDA a fixed number of precursor ions whose m/z values are recorded in a survey scan are selected using predetermined rules and are subjected to a second stage of mass selection in an MS/MS analysis.

In targeted data acquisition platforms, selective reaction monitoring/multiple reaction monitoring (S/MRM) is often used. The method exploits the capability of the first and the third quadrupole in a triple quadrupole mass spectrometer to act as mass filters for the iterative isolation of a precursor ion and a fragment ion derived from the targeted precursor, also known as a transition. In a typical S/MRM experiment, the signal of three to six transitions per targeted MHC peptide ligand is recorded over the chromatographic elution profile of the targeted peptide.

DIA is a method of molecular structure determination in which all ions within a selected m/z range are fragmented and analyzed in a second stage of tandem mass spectrometry.

In one embodiment, HLA peptides are loaded onto a nanoViper Acclaim™ PepMap™100 C18 trap column (75 µm i.d.×2 cm, 3 µm, 100 Å, Thermo) and separated using a nanoViper Acclaim™ PepMap™ RSLC C18 column (75 µm i.d.×25 cm, 2 µm, 100 Å, Thermo) retrofitted with a New Objective SilcaTip (7 cm) with a distal conductive coating at inlet end of the emitter. An elution gradient can be delivered by an EASY-nLC™ 1200 HPLC system (Thermo) at 300 nL/min. In one embodiment, A 120-minute elution gradient with mobile phase A (0.1% formic acid in $H_2O$) and B (0.1% formic acid in 80% ACN) can be as follows (% B): 2 to 3% at 3 min, linear to 35% at 100 min, and linear to 45% at 123 min. The peptides eluted from the column can be ionized via Flex ion source at 1.7 kV and analyzed by the Thermo Fusion™ Lumos™ Tribrid™ mass spectrometer (Thermo) using Xcalibur 4.1 (version 4.1.31.9—Thermo Scientific).

C. Discovery Mode

In one embodiment, ionized peptides are isolated, for example by LC chromatography, and are continuously introduced into the mass spectrometer to produce a survey scan of the isolated peptides. The peptides can be sequenced continuously in discovery mode, for example for 60, 70, 80, 90, 100, 110, or 120 minutes, starting with the most abundant peptides and working to lesser abundant peptides. The peptides are separated within a quadrupole mass analyzer based on their mass-to-charge ratio (m/z). In one embodiment, the survey scans can be carried out in the high field Orbitrap analyzer with resolution at 60,000 and automatic gain control targeted at $1.0^5$ ions over a mass range of 300-1500 m/z and maximal ion fill time of 100 ms. $MS^2$ of the top discovery ions can be performed with Higher-energy collisional dissociation (HCD), and can be scanned in the Orbitrap with a dynamic exclusion window of 6 s. For each $MS^2$ scan, $10^4$ ions can be accumulated with a maximal fill time of 100 ms. In one embodiment, the discovery mode can detect 3,000-4,000 peptides in a 120 minute scan period.

A targeted mass filter can be applied to monitor a priority list of spiked-in heavy peptides or otherwise labeled Human Leukocyte antigens (HLA) associated peptides of interest during the discovery mode. In one embodiment, up to $X_n$ priority targets can be included in the priority list, where n is any integer, for example n=10, 20, 30, 40, 50 or more. In one embodiment, the discovery mode program is constantly running and recording mass data. The discovery mode typically runs until one of the monitored spiked-in heavy peptides is detected. In one embodiment, the spiked-in heavy peptides have a different mass-to-charge ratio (m/z) compared to the unlabeled isolated peptide. The shift in m/z triggers a switch (or "toggle") from discovery mode to targeted trigger mode. For example, labeled lysine increases the m/z by 3.509 and labeled valine increases the m/z by 3.007.

D. Targeted Trigger Mode

In one embodiment, the targeted trigger mode (Priority 1) is activated once the spectra of a monitored heavy peptide, for example leucine (L)($^{13}C_6^{15}N_1$), is detected by the mass filter, and the sample is sent to the Orbitrap (FIG. 9) for $MS^2$. In one embodiment, only the target mass+/−1.2 daltons is allowed through the quadrupole to the Orbitrap. During acquisition of triggered-offset, the maximal ion fill time can be changed to 400 ms without any dynamic exclusion. By extending the fill time to at least 400 ms, low copy number peptides can accumulate in the Orbitrap and produce more robust spectra. The acquisition remains in the targeted trigger mode until the heavy peptide is undetectable by the mass filter and then the program is returned to the discovery mode until the detection of the next spiked-in heavy peptide.

Peaks® software (version 8.5) or in-house generated databases can be used to process the raw MS files prior to searching against the Human Uniprot database (UniProt Consortium). The peptide false discovery rate (FDR) can be set at 5% and the protein ID can be accepted with an ion score of 20 or above. HLA binding affinities can be predicted by Net MHC 3.4 server (CBS). An affinity score ≤50 nM represents that the peptide is a strong binder and an affinity ≤500 nM shows that it is a weak binder. If a score is >500 nM, then that peptide is considered a non-binder.

Figure 4:
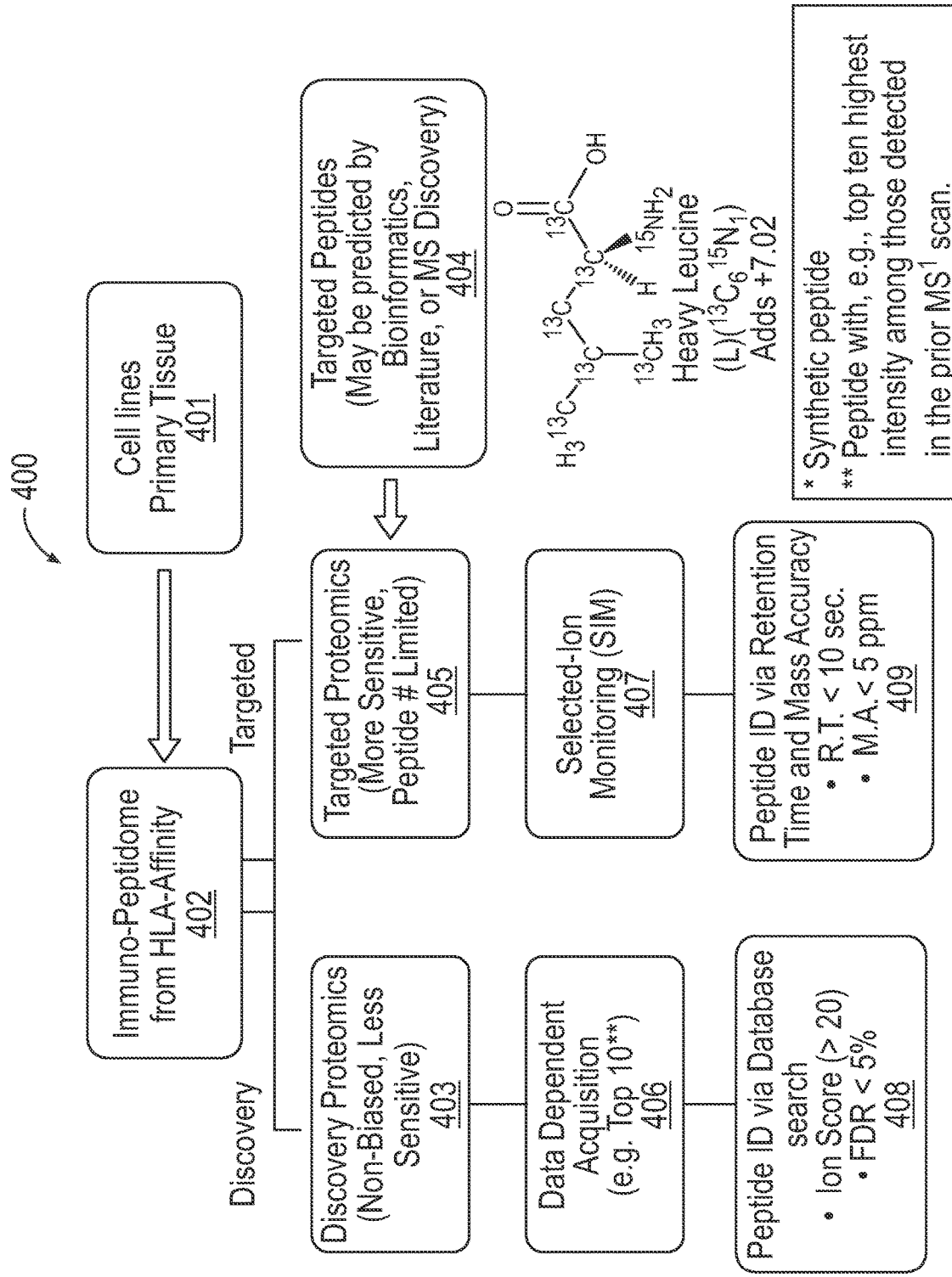
FIG. 4 is a flow diagram of an exemplary method showing discovery and targeting approaches for identifying peptides-in-groove (PiG) targets that includes using the synthetic peptide heavy leucine (L)($^{13}C_6^{15}N_1$). For certain uses of the synthetic peptide provided by this method: Retention time for the heavy peptide may be exactly the same as endogenous peptide; Exact mass difference of heavy amino acid needs to be seen to confirm; and Verification of shifted B and Y ions may also be used in order to have additional confirmation.

FIG. 4 shows a flow diagram of an exemplary method of the invention. Cell lines or tissue, for example tissue from a tumor, can be used in this immune-peptidome HLA affinity method.

The method is divided into discovery and targeted branches or modes. The discovery mode is identified as a non-biased and less sensitive method. Data is dependent on acquisition. The peptides are identified via a database search.

In the targeted branch or mode, peptides that bind to MHC are predicted using bioinformatics, literature, and mass spectrometry discovery. In the targeting mode, the number of peptides is limited and select ion monitoring is employed. Peptides are identified via retention time and mass accuracy. The targeted approach requires a synthetic peptide incorporating a label, e.g., heavy leucine. With regard to the synthetic peptide, retention time for the heavy peptide is exactly the same as endogenous peptide, exact mass difference of heavy amino acid needs to be seen to confirm, and verification of shifted B and Y ions are also used to have additional confirmation. In some embodiments, the HPV E7 peptide YMLDLQPET (SEQ ID NO:2) is used as the labeled heavy peptide, in which the double underlined amino acid is heavy leucine.

Figure 5:
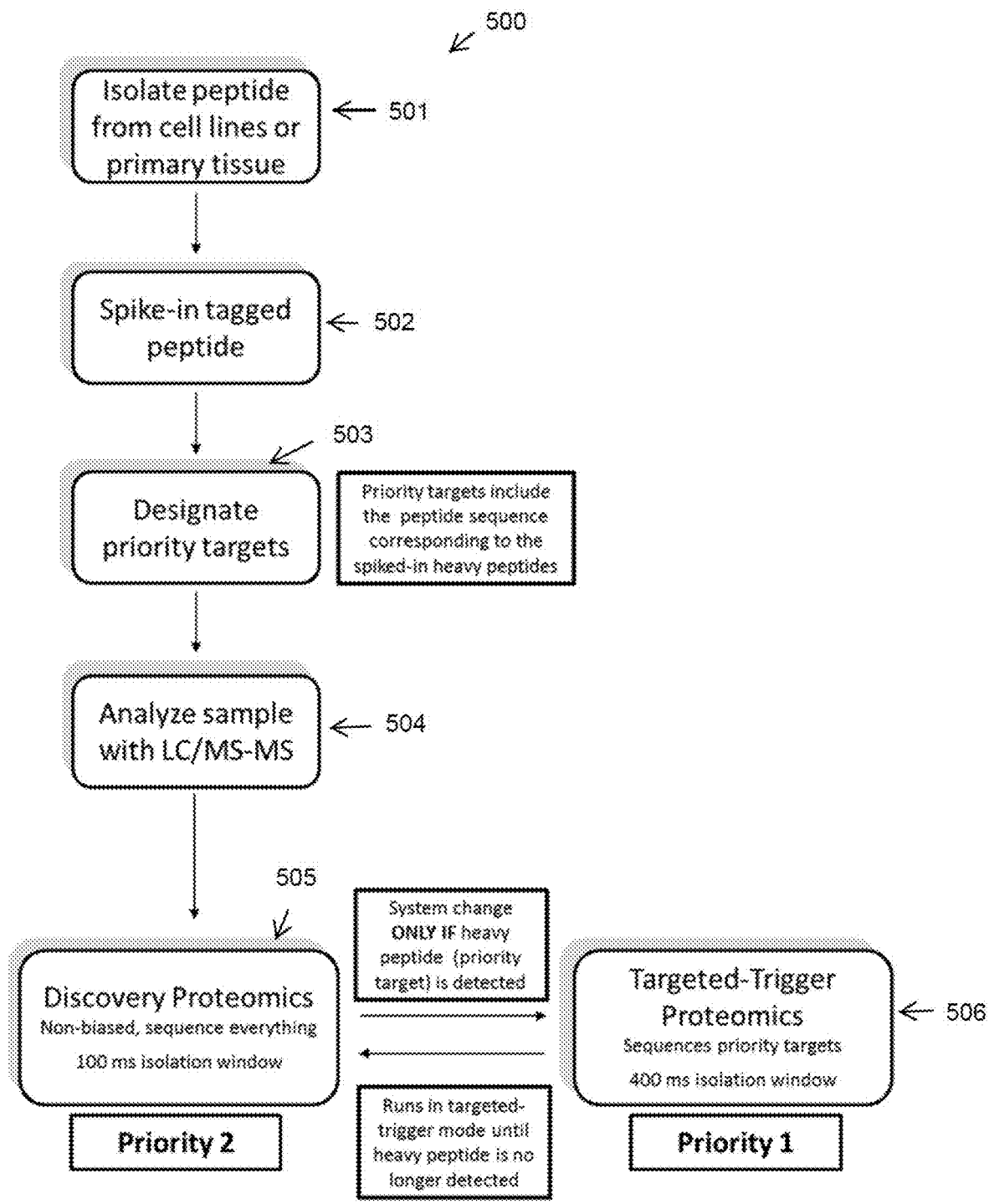
FIG. 5 is an exemplary diagram of combination of discovery and targeted approaches for identifying peptide targets referred to as the "Targeted-Trigger Method".

FIG. 5 is a flow diagram of the combination of an exemplary discovery and targeted approaches referred to as the Targeted-Trigger Method. In this method, the lysate from cancerous tissue or cancer cell lines are processed in discovery mode until the system detects the heavy tagged peptide. Once the heavy peptide is detected, the system is triggered to fully scan the peptides coming through the system. If no heavy peptides are detected, the system operates in the discovery mode.

FIG. 2A shows an exemplary method for obtaining peptides for mass spectrometry analysis. Step 201 begins with producing a cell lysate starting with about 20, 30, or 40 mgs or $1×10^8$ cells. The lysate is passed through an affinity column such as an anti-HLA Class I pan monoclonal column to isolate peptide-HLA complexes 203. The peptide-HLA complexes 203 are spiked with a heavy peptide that is known to bind to HLA-I complex or is of a desired mass. The spiked sample is then passed through a reverse phase column, for example, a C18 Sep-Pak column, and peptides 205 for mass spectrometry analysis are selectively eluted.

Figure 3:
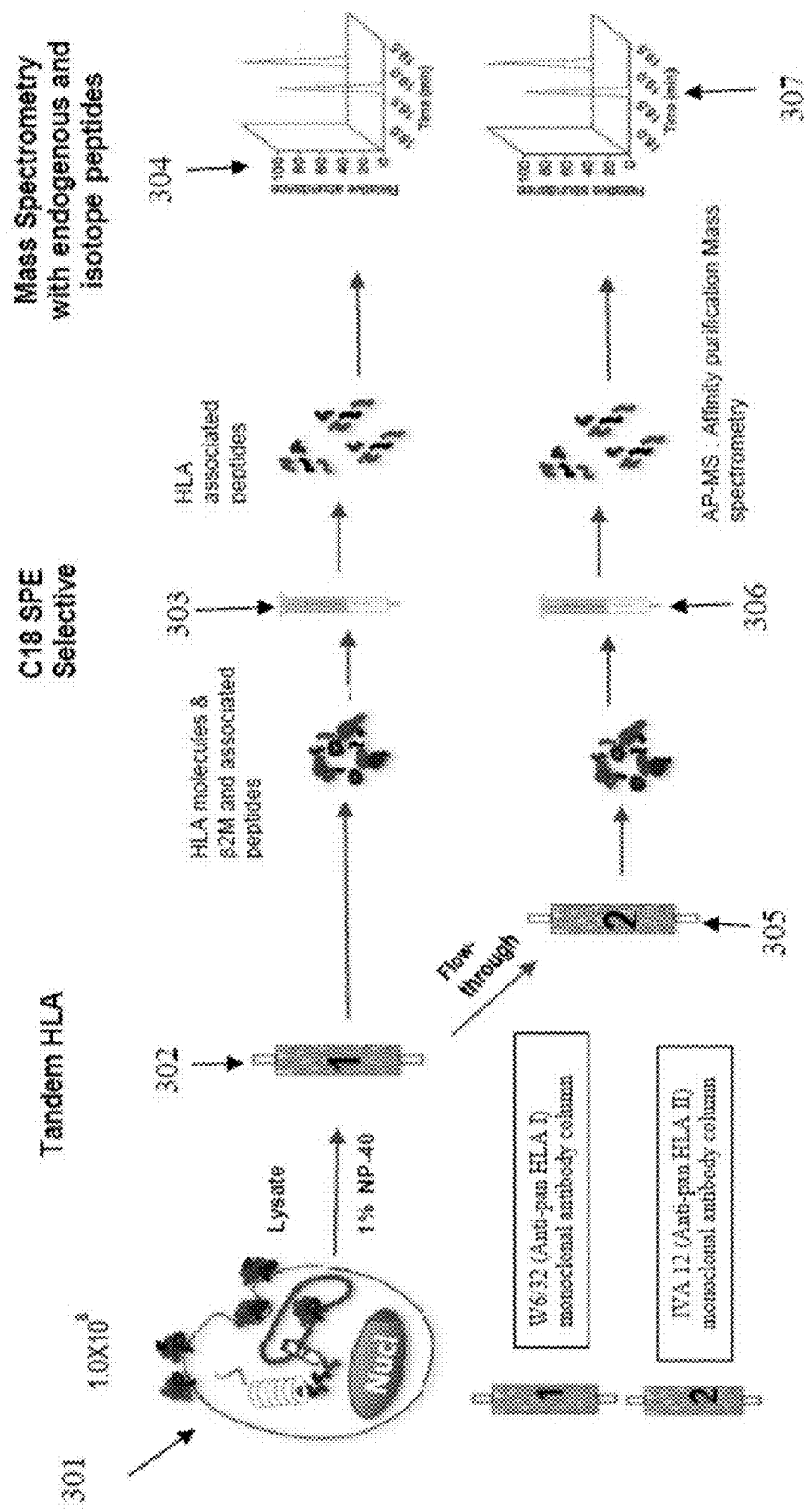
FIG. 3 is another exemplary method for identifying peptides-in-groove (PiGs) using two affinity columns in order to maximize tissue or cell samples for mass spectrometry identification of HLA Class I and HLA Class II-associated peptides in tandem.

FIG. 3 shows a similar process to FIG. 2A differing in that the process in FIG. 3 includes separating the peptide-HLA complexes formed between peptides and HLA-I or HLA-II. The process depicted in FIG. 3 begins with step 301 obtaining a cell lysate from about $1.0×10^8$ cells. The lysate is passed through an anti-HLA-I monoclonal antibody column 302 or an anti-pan HLA-II monoclonal antibody column 305 to obtain HLA molecules and β2M and associated peptides. The HLA molecules and β2M and associated peptides are then passed through a C18 SPE selective column 303 to isolate the HLA associated peptides. Alternatively, the HLA molecules and β2M and associated peptides are passed through an affinity purification column 306 to produce affinity purified HLA associated peptides.

The peptides are spiked with a known labeled peptide and subjected to mass spectrometry analysis to identify the peptides that have the same or similar mass of the labeled peptide.

FIGS. 4 and 5 show additional exemplary methods for target triggered analysis and identification of peptides that bind to HLA-I or HLA-II. Process 400 begins with cell lines or primary tissue in step 401. The cell lines or primary tissue is processed through an HLA affinity purification step in 402. Process 400 includes a discovery mode and a targeted mode. In step 403 of the discovery mode, peptides are processed by mass spectroscopy in non-biased and less sensitive manner. In step 406, the top 10 peptides are identified and identities are searched in a protein/peptide database in step 408. Process 400 also includes a targeted mode 404 in which peptide selected via database searching, literature searching, or MS discovery for possible binding to HLA-I or HLA-II are labeled, for example with a heavy amino acid. The labeled peptide is spiked into the sample processed in step 402. In step 407, selected ions are monitored. In step 409, the peptides are identified via retention time and mass spectrometry.

FIG. 5 depicts process 500, which begins with isolated peptides from cell lines or tissues in step 501. A labeled (e.g., heavy) peptide known or suspected to bind to HLA-I or HLA-II is added to the isolated peptides. In step 503, target peptides are designated, including the peptide corresponding to the spiked-in heavy peptide. In step 504, the sample is analyzed with LC/MS-MS to determine the amino acid sequence of the peptides by either a discovery mode 505 that is non-biased and identifies all peptides in the sample in about 100 ms or the sample is analyzed in a target-trigger mode 506 that identifies only the priority peptides in about 400 ms. Step 506 is only triggered if heavy peptide is detected by MS and runs until heavy peptide is no longer detected. Once heavy peptide is no longer detected, the system changes to the discovery mode 505.

In one embodiment, the disclosed systems and methods can be used to characterize immune markers expressed on T cells, for example tumor infiltrating leukocytes (TILs), in processed tumor samples. For example, tumor tissue can be analyzed for expression of PD-1, PD-L1, PD-L2, CTLA4, TIGIT, GITR, LAG3, or other immune checkpoint molecules on infiltration leukocytes in the tumor, and subsequently inform decisions. Profiles of T cell subsets may also be identified by assessing markers of T cells such as CD4, CD8, CD3, CD69, CD45R0, CCR7, CD28, CD95, and others. The presence of certain immune markers (profiling both T cell markers and checkpoint markers) presented on TILs in the tumor environment may be a measure of the level of activation of antigen specific TILs needed to eliminate tumor burden.

Post-Translational Modifications

In one embodiment, the disclosed systems and methods can also be used to characterize normal (i.e., unmodified) proteins with post-translational modifications (PTMs) and/or proteins with aberrant post-translational modifications. The association of aberrant PTM patterns with diseases such as cancers has been described in, for example, Marino, F; et al., *J. Proteome Res.* 2017, 16, 34-44; Malaker et al. *Cancer Immunol Res.* 2017 May; 5(5): 376-384; and Skipper et al., J Exp. Med., the entire contents of each of which are expressly incorporated herein by reference. For example, modified tyrosinase TyrD369-377 provides a peptide site that interacts differently with HLA because a carbohydrate side chain on an asparagine residue interferes with HLA binding. The TyrD peptide is more readily presented by HLA on the cells, and therefore was identified as a tumor target.

Post-translational modifications that can be detected by the systems and methods described herein include, but are not limited to, methylation, Di-methylation, deamidation, phosphorylation, citrullination, and acetylation. PTMs can be detected by shifts of value in mass spectrum (mass shift). For example, methylation on lysine (K) or arginine (R) can have a mass shift of about 14.0156; Di-methylation on lysine (K) or arginine (R) can have a mass shift of about 28.0313; deamidation of asparagine (N) or glutamine (Q) can have a mass shift of about 0.9840; phosphorylation on serine (S), threonine (T), or tyrosine (Y) can have a mass shift of about 79.9664; citrullination of arginine (R) can have a mass shift of about 0.9840; and acetylation of lysine (K) can have a mass shift of about 42.0106. Other indices of PTMs known in the art can also be used to characterize PTMs on the peptides identified using the systems and methods described herein.

The patterns of PTMs on peptides may be determined by the targeted trigger method. For example, "heavy" spiked-in peptide(s) can be used, and due to increased sensitivity of the heavy spike-in method combined with the ability to toggle back and forth to discovery mode, novel peptides with post-translationally modified amino acids, and novel and rare PTMs can also be confirmed while maintaining the ability to capture information for the totality of the immunopeptidome for the single tissue sample in a single test. The peptides identified or confirmed in a sample can serve as immunogens for making biotherapeutics such as antibodies, bispecific antibodies, antibody-drug conjugates, TCRs, vaccines, and CAR T cells.

Thus, the systems and methods described herein can be used to distinguish PTM peptides from unmodified peptides, or to distinguish peptides with different levels of PTMs from normal PTM peptides. In one embodiment, tumor tissues have PTM peptides that are not identified in normal tissues. In one embodiment, tumor tissues have peptides without PTM(s) that are found in normal tissues. In one embodiment, tumor tissues have peptides with different levels of PTMs compared to normal tissues.

III. Systems

Mass spectroscopy platforms for immunopeptidome discovery are known in the art. See for example Caron, E., et al., Molecular & Cellular Proteomics 14.12 (2015) which is incorporated by reference in its entirety. One embodiment provides an LC-MS/MS system that is programmed to increase the scan duration at or near the m/z of a peptide of interest, e.g., the heavy peptide, when the peptide of interest is detected. Typically the peptide of interest is labeled with a detectable label as discussed above. In one embodiment the LC-MS/MS system is a Orbitrap Fusion™ Lumos Tribrid™ Mass Spectrometer programmed with a trigger filter that increase the scan duration at or near the m/z of a peptide of interest when the peptide of interest is detected.

EXAMPLES

Example 1: Simultaneous Profiling and Validation of HLA-Associated Peptides (Immunopeptidomes) by Discovery Combined with Targeted Trigger LC-MS Approach Materials and Methods
Sample Preparation Each fresh frozen procured tissue was first powdered on dry ice and was then lysed in NP-40 buffer with HALT protease and phosphatase inhibitors (Thermo Scientific, cat. 78442) on ice. The solution was further disrupted with a tissue raptor to generate a homogenous lysate. The lysate was rotated for 1 hour at 4° C. followed by a 30 minute centrifugation at 20,913 g at 4° C. Lysates were then passed over an in-house pan HLA-Class I affinity column (1 ml column, 4 mg of total antibody on beads). Captured HLA-peptide complexes were eluted with 4 mL of glycine pH 2.5. One mL of 0.1% trifluoroacetic acid (TFA) was added to the eluant before passing through a Sep Pak tC18 1 CC cartridge (Waters, Cat. WAT054960). The cartridge was washed 3 times with 1 mL of 0.1% TFA. The bound peptides were selectively eluted from the tC-18 cartridges using 30% acetonitrile (ACN) in 0.1% TFA. The eluted peptides were speedvac dried and re-suspended into 20 µl of 0.1% TFA (along with heavy spike-in peptides) for LC-MS/MS analysis. (See FIG. 1).

LC-MS/MS Analysis of HLA Class I Peptides (Discovery-Targeted Trigger Method)

HLA peptides prepared as described above were loaded onto a nanoViper Acclaim PepMap100 C18 trap column (75 µm i.d.×2 cm, 3 µm, 100 Å, Thermo) and were separated using a nanoViper Acclaim PepMap RSLC C18 column (75 µm i.d.×25 cm, 2 µm, 100 Å, Thermo) retrofitted with a New Objective SilcaTip (7 cm) with a distal conductive coating at inlet end of the emitter. The gradient was delivered by an EASY-nLC 1200 HPLC system (Thermo) at 300 nL/min. A 120-minute elution gradient with mobile phase A (0.1% formic acid in $H_2O$) and B (0.1% formic acid in 80% ACN) was as follows (% B): 2 to 3% at 3 minutes, linear to 35% at 10 minutes, and linear to 45% at 123 minutes. The peptides eluted from the column were ionized via Flex ion source at 1.7 kV and analyzed by the Thermo Fusion Lumos Tribrid mass spectrometer (Thermo) using Xcalibur 4.1 (version 4.1.31.9—Thermo Scientific).

Discovery Mode. Survey scans were carried out in the high field Orbitrap analyzer with resolution at 60,000 and automatic gain control targeted at $1.0^5$ ions over a mass range of m/z 300-1500 and maximal ion fill time of 100 ms. $MS^2$ of the Top N discovery ions were performed with Higher-energy collisional dissociation (HCD), and were scanned in the Orbitrap with a dynamic exclusion window of 6 s. For each $MS^2$ scan, $10^4$ ions were accumulated with a maximal fill time of 100 ms. A targeted mass filter was applied to monitor a list of spiked-in heavy peptides of interested Human Leukocyte antigens (HLA) associated peptides during the discovery mode.

Targeted Trigger Mode. Once the spectra of a monitored heavy peptide was detected by the mass filter, the $ddMS^2$ scan on the corresponding endogenous (light) peptide would be triggered by the "isolation offset". During acquisition of triggered-offset, the maximal ion fill time was changed to 400 ms without any dynamic exclusion. The acquisition remained in the targeted trigger mode until the heavy peptide was undetectable by the mass filter and then returned to the discovery mode until the detection of the next spike-in heavy peptide.

Results

Peaks® software (version 8.5) was used to process the raw MS files prior to searching against the Human Uniprot database (UniProt Consortium) or in-house generated databases. The peptide false discovery rate (FDR) was set at 5% and the protein ID was accepted with an ion score of 20 or above. HLA binding affinities were predicted by Net MHC 3.4 server (CBS). An affinity score ≤50 nM represents that the peptide is a strong binder and an affinity ≤500 nM shows that it is a weak binder. If a score is >500 nM, then that peptide is considered non-binder.

Example 2: HPV16 $E7_{11-19}$ Peptide was Detected with an Estimated 64 Copies on a Human Cervical Tumor Sample $1 \times 10^8$ Caski cells (a well-known cervical tumor cell line) were used as a source of tumor peptides, and Caski cells were used in comparison to a human cervical tumor patient sample. The cells were processed according to the methods shown in FIGS. 1, 2A, and 3-5.

Figure 6A:
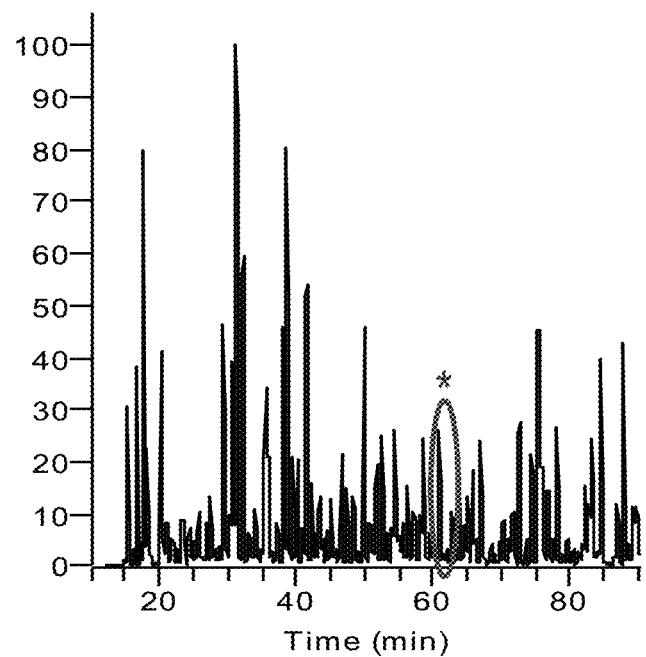
FIG. 6A is a chromatograph showing the identification of HPV16 E7$_{11-19}$ peptide on Caski cells.
Figure 6B:
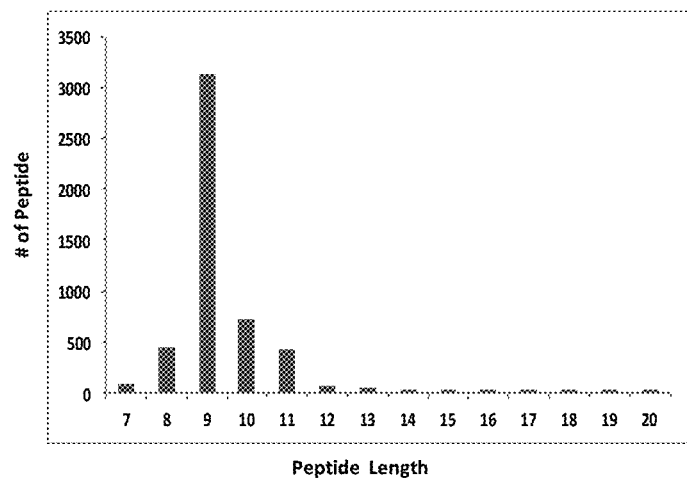
FIG. 6B is a bar chart of number of peptides detected versus length of peptide detected on Caski cells.
Figure 6C:
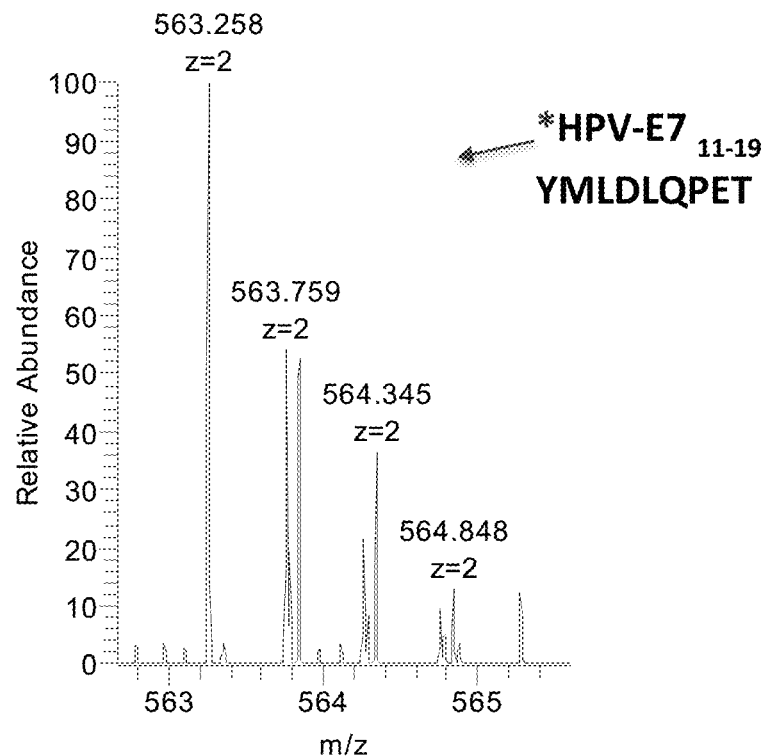
FIG. 6C is the mass spectrum of the peptides detected by mass spectrometry on Caski cells.

FIGS. 6A-6C represent screening Caski cells with spiked (heavy) HPV-$E7_{11-19}$ peptide using the targeted trigger discovery mode. HPV-$E7_{11-19}$ refers to amino acids 11 to 19 of the Human papillomavirus type 16 Protein E7 having the following amino acid sequence: YMLDLQPET (SEQ ID NO:2). FIG. 6A is a LC-MS graph of the base peak chromatogram FIG. 6B is a bar graph of peptides identified from the cell lysate separated as described above. FIG. 6B shows the peptide length distribution of the identified peptides. 4,975 peptides were identified and sequenced, with the majority being 9-11 peptides in length. FIG. 6C shows that HPV-E7 was detected on Caski cells using the targeted trigger mode. In FIG. 6C, the peak representing the endogenous (non-labeled) peptide is labeled as 563.258.

In contrast, when the same sample was screened by discovery mode only (data not shown) the discovery mode was not sensitive enough to identify the HPV-$E7_{11-19}$ peptide.

Figures 7A, 7B:
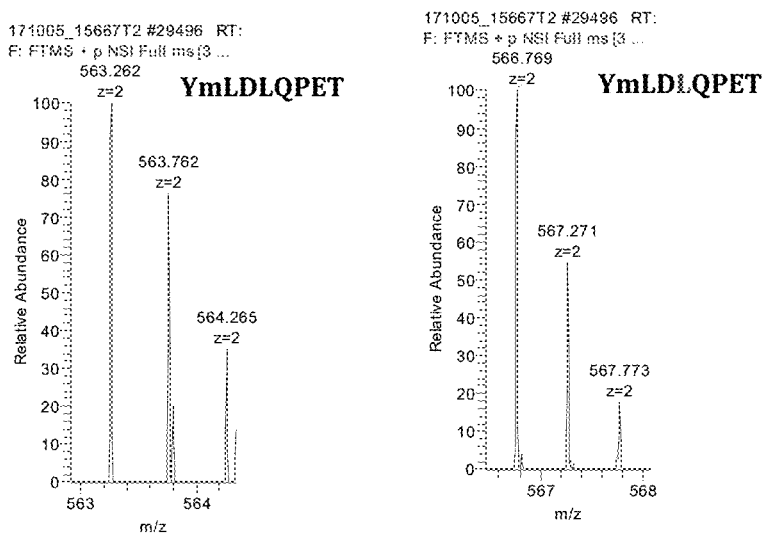
FIGS. 7A and 7B are mass spectra showing HPV16 E7$_{11-19}$ peptide was detected with an estimated 64 copies on a human cervical tumor sample. Heavy peptide is shown in FIG. 7B and light peptide is shown in 7A.
Figure 7C:
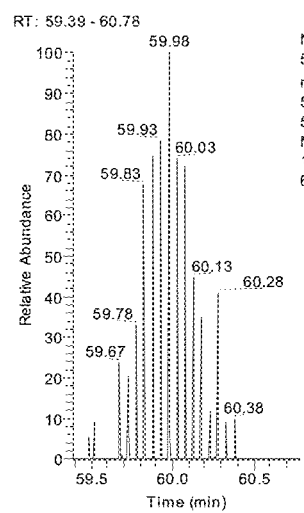
FIGS. 7C and 7D are corresponding chromatograms for FIGS. 7A and 7B, respectively.
Figure 7D:
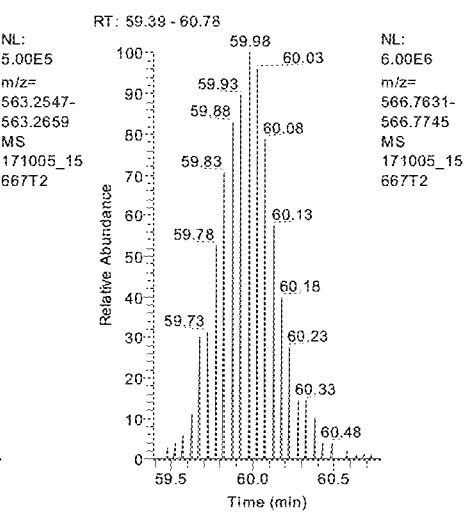

FIGS. 7A and 7B are mass spectra that show HPV16 $E7_{11-19}$ peptide was detected with an estimated 64 copies on a human cervical tumor patient sample. "Heavy" (spiked in) peptide is shown in FIG. 7B and "light" (endogenous) peptide is shown in 7A. FIGS. 7C and 7D are corresponding chromatograms for FIGS. 7A and 7B.

Example 3: Detection of Numerous HLA-Peptides from Human Melanoma Tumor Samples Materials and Methods As discussed above in e.g., Example 1 and the Figures.

Results

Table 1 shows that several hundred to 1000+ HLA-associated peptides were detected and identified in each of 10 human tumor samples. Peptides were detected from melanoma-specific proteins including PRAME, MAGE-A4, MART-1, tyrosinase, and PMEL (gp100). The data enables strategies such as choosing the most abundant peptide, or choosing among tumor-specific peptides (not presented on normal tissue).

TABLE 1

10 Patient melanoma samples (# peptides detected by mass spec)

Patient Melanoma Samples (# of Detected Peptides)

| Length | 1 | 2 | 3 | 4 | 5 | 6 | 7 | 8 | 9 | 10 |
|---|---|---|---|---|---|---|---|---|---|---|
| 7 | 235 | 71 | 65 | 200 | 81 | 45 | 105 | 156 | 144 | 117 |
| 8 | 410 | 126 | 122 | 442 | 161 | 53 | 321 | 189 | 138 | 168 |
| 9 | 1170 | 245 | 219 | 993 | 498 | 139 | 718 | 786 | 540 | 1099 |
| 10 | 757 | 109 | 127 | 449 | 178 | 69 | 372 | 345 | 364 | 385 |
| 11 | 555 | 90 | 86 | 290 | 121 | 36 | 299 | 206 | 234 | 253 |
| 12 | 271 | 65 | 49 | 125 | 66 | 18 | 139 | 109 | 107 | 115 |
| 13 | 163 | 39 | 34 | 91 | 46 | 24 | 77 | 65 | 42 | 79 |
| 14 | 104 | 24 | 21 | 49 | 25 | 19 | 64 | 54 | 17 | 50 |
| 15 | 103 | 13 | 16 | 42 | 25 | 17 | 35 | 30 | 11 | 46 |
| 16 | 78 | 14 | 10 | 48 | 20 | 12 | 41 | 27 | 10 | 49 |
| 17 | 61 | 6 | 10 | 33 | 10 | 6 | 32 | 20 | 4 | 43 |
| 18 | 50 | 3 | 11 | 31 | 11 | 5 | 13 | 9 | 4 | 32 |
| 19 | 45 | 2 | 6 | 26 | 8 | 2 | 16 | 6 | 0 | 29 |
| 20 | 44 | 2 | 3 | 20 | 6 | 1 | 10 | 4 | 1 | 21 |
| Total | 4046 | 809 | 779 | 2839 | 1256 | 446 | 2242 | 2006 | 1616 | 2486 |

A selected peptide, in association with (or tethered to) its HLA molecule, may be provided as an immunogen for the generation of therapeutic antibodies (see for example VELOCIMMUNE® technology U.S. Pat. No. 6,596,541, Regeneron Pharmaceuticals) or therapeutic TCRs (see WO2016164492, published Oct. 13, 2016), or any other known method for generating therapeutic antigen-binding proteins, e.g., monoclonal antibodies, bispecific antibodies, soluble or membrane-bound TCRs, chimeric antibodies and TCRs, chimeric antigen receptors (CARs) and/or the variable domains thereof. Such antigen-binding proteins may bind to a conformational epitope of the HLA presented peptide.

Example 4: HPV16 $E7_{11-19}$ Peptides Detected in Cervical Tumors Using Targeted Trigger Method Materials and Methods As discussed above, in, e.g., Example 1 and the Figures. The targeted trigger method was used in this Example. Fifty-six cervical tumor samples were analyzed.

Results

Table 2 shows that HPV16 $E7_{11-19}$ was detected about 73% of HLA-A02(+) HPV16 E7(+) cervical tumors using the disclosed systems and methods. Out of 56 cervical tumors analyzed, 25 (~45%) were HLA-A02(+); 34 (~61%) were HPV16 E7(+); and 15 (~27%) were both HLA-A02(+) and HPV16 E7(+).

The HPV16 $E7_{11-19}$ peptide, YMLDLQPET (SEQ ID NO:2), was consistently detected on the HLA-A02(+) and HPV16 E7(+) cervical cancer cell tumors with and without interferon gamma treatment (which increases HLA expression and peptide presentation), using the targeted trigger method as described herein.

With the addition of a heavy peptide ("spiked-in"), and utilizing the targeted trigger approach to test the small sample only once, the relative abundance of endogenous (i.e., non-heavy) HPV16 $E7_{11-19}$ peptide on the cell surface can be estimated while also obtaining a pool of additional immunopeptidome information from a single run.

TABLE 2

| Tumor Tissue | Tumor Sample Number | PCR HLA-A02 | HPV16 E7 | LC-MS HPV16 E7 11-19 | 9 mers HLA-A02* | Total |
|---|---|---|---|---|---|---|
| Cervical | 1 | Yes | ++++ | Detected | 1188 | 3312 |
| Cervical | 2 | Yes | ++++ | Detected | 856 | 2642 |
| Cervical | 3 | Yes | +++++ | Detected | 739 | 2661 |
| Cervical | 4 | Yes | +++ | Detected | 503 | 2221 |
| Cervical | 5 | Yes | +++++ | Detected | 726 | 3014 |
| Cervical | 6 | Yes | ++++ | Detected | 1119 | 3590 |
| Cervical | 7 | Yes | ++++ | Detected | 1383 | 2492 |
| Cervical | 8 | Yes | +++++ | Detected | 1873 | 4599 |
| Cervical | 9 | Yes | ++++ | Detected | 2044 | 4601 |
| Cervical | 10 | Yes | +++++ | Detected | 2021 | 4266 |
| Cervical | 11 | Yes | +++++ | Detected | 1683 | 4457 |
| Cervical | 12 | Yes | +++++ | Not Detected | 2218 | 3501 |
| Cervical | 13 | Yes | +++++ | Not Detected | 10 | 2297 |
| Cervical | 14 | Yes | ++ | Not Detected | 490 | 2456 |
| Cervical | 15 | Yes | ++++ | Not Detected | 788 | 2153 |

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

The invention claimed is:

1. A mass spectrometry method, the method comprising:
   obtaining a sample comprising unlabeled isolated peptides from an MHC-I or HLA-I complex or an MHC-II or HLA-II complex;
   adding one or more labeled peptides to the sample to form a single mixed sample comprising the labeled peptides and the unlabeled isolated peptides;
   processing the single mixed sample with an LC-MS/MS system, comprising:
   i) processing the single mixed sample in discovery mode to detect and identify one or more of the unlabeled isolated peptides and the one or more labeled peptides in the single mixed sample;
   ii) wherein, when the one or more labeled peptides are detected, processing the same mixed sample with the LC-MS/MS system in targeted mode, thereby detecting and identifying the one or more labeled peptides; and
   iii) wherein the LC-MS/MS system toggles between processing the mixed sample in discovery mode and processing the mixed sample in targeted mode in the same LC-MS/MS run,
   thereby detecting both labeled and unlabeled peptides in the single mixed sample.

2. The method of claim 1, further comprising:
   iv) wherein, when the one or more labeled peptides is no longer detected, processing the mixed sample with the LC-MS/MS system in discovery mode to detect and identify one or more of the unlabeled isolated peptides and the one or more labeled peptides in the mixed sample.

3. The method of claim 2, further comprising:
   v) wherein, when the one or more labeled peptides are detected, processing the mixed sample with the LC-MS/MS system in targeted mode, thereby detecting and identifying the one or more labeled peptides.

4. The method of claim 3, wherein steps iii) and iv) and v) are repeated 2 times, 3 times, 4 times, 5 times, 6 times, 7 times, 8 times, 9 times, or 10 times.

5. The method of claim 1, wherein the obtaining step comprises isolating the unlabeled peptides from an MHC-I or HLA-I complex or an MHC-II or HLA-II complex.

6. The method of claim 5, wherein the isolating comprises affinity chromatography and/or column chromatography.

7. The method of claim 5, wherein the isolating comprises isolating by affinity chromatography the MHC-I or HLA-I complex or the MHC-II or HLA-II complex obtained from a tissue lysate; and
   separating peptides from the complexes by column chromatography to produce the unlabeled isolated peptides.

8. The method of claim 5, wherein the isolating comprises passing a tissue lysate through an affinity chromatography column to produce a flow-through;
   eluting the column to produce a first eluate, wherein the first eluate comprises MHC-peptide complexes and beta2M associated peptides;
   passing the flow-through through a second affinity chromatography column to obtain a second eluate comprising MHC-peptide complexes and beta2M associated peptides; and
   independently eluting the peptides from the first and second eluates to produce unlabeled isolated peptides.

9. The method of claim 6, wherein the affinity chromatography comprises an anti-HLA I column.

10. The method of claim 6, wherein the second affinity column comprises a pan HLA II column.

11. The method of claim 6, wherein the column chromatography comprises use of a C18 reverse phase chromatography column.

12. The method of claim 1, wherein the sample comprising unlabeled isolated peptides is a tissue lysate.

13. The method of claim 12, wherein the tissue lysate is produced using chemical and/or physical techniques.

14. The method of claim 13, wherein the tissue lysate is produced from a tissue using a detergent.

15. The method of claim 13, wherein the tissue lysate is produced from prostate tissue, breast tissue, testicular tissue, thyroid, colon tissue, ovarian tissue, pancreatic tissue, nervous tissue, bone, bone marrow, peripheral blood mononuclear cells, metastatic tissue, cancer cell lines, biopsies, or ocular tissue.

16. The method of claim 1, further comprising determining an amino acid sequence of the unlabeled isolated peptides detected.

17. The method of claim 1, wherein a sequence of the unlabeled isolated peptides is determined in an m/z range that includes the m/z of the one or more labeled peptides.

18. The method of claim 1, wherein the labeled peptides are peptides labeled with heavy leucine, isoleucine, valine, threonine, lysine, tyrosine, phenylalanine, glycine, alanine, arginine, aspartic acid, or proline.

19. The method of claim 17, wherein the heavy leucine is $(L)(^{13}C_6^{15}N_1)$.

20. The method of claim 1, wherein the method quantifies peptides present at a level of 30, 40, or 50 copies per cell or more.

* * * * *

UNITED STATES PATENT AND TRADEMARK OFFICE
CERTIFICATE OF CORRECTION

| | | |
|---|---|---|
| PATENT NO. | : 11,747,340 B2 | Page 1 of 1 |
| APPLICATION NO. | : 16/361342 | |
| DATED | : September 5, 2023 | |
| INVENTOR(S) | : Robert Salzler | |

It is certified that error appears in the above-identified patent and that said Letters Patent is hereby corrected as shown below:

In the Claims

At Column 25, Line number 53, Claim number 4, delete "iii) and"

Signed and Sealed this
Twenty-eighth Day of November, 2023

*Katherine Kelly Vidal*

Katherine Kelly Vidal
*Director of the United States Patent and Trademark Office*